United States Patent
Qu et al.

(10) Patent No.: US 10,994,028 B2
(45) Date of Patent: May 4, 2021

(54) SCALABLE MANUFACTURING PROCESS TO PRODUCE RECOMBINANT LENTIVIRAL VECTORS IN SERUM-FREE SUSPENSION CELL CULTURE SYSTEM

(71) Applicant: The Children's Hospital of Philadelphia, Philadelphia, PA (US)

(72) Inventors: Guang Qu, Sicklerville, NJ (US); John Fraser Wright, Princeton, NJ (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 1 day.

(21) Appl. No.: 15/699,613

(22) Filed: Sep. 8, 2017

(65) Prior Publication Data

US 2017/0368201 A1    Dec. 28, 2017

Related U.S. Application Data

(63) Continuation of application No. 14/216,778, filed on Mar. 17, 2014, now abandoned.

(60) Provisional application No. 61/787,818, filed on Mar. 15, 2013.

(51) Int. Cl.
*C12N 7/02* (2006.01)
*C12N 7/00* (2006.01)
*C12N 15/867* (2006.01)
*A61K 48/00* (2006.01)

(52) U.S. Cl.
CPC ............ *A61K 48/0091* (2013.01); *C12N 7/00* (2013.01); *C12N 2740/15043* (2013.01); *C12N 2740/15051* (2013.01)

(58) Field of Classification Search
None
See application file for complete search history.

(56) References Cited

U.S. PATENT DOCUMENTS

| | | | |
|---|---|---|---|
| 5,869,445 A | 2/1999 | Cheever et al. | |
| 6,544,769 B1 | 4/2003 | Frei et al. | |
| 2003/0008374 A1 * | 1/2003 | Trono | A61K 35/17 435/235.1 |
| 2003/0157070 A1 | 8/2003 | Jolly | |
| 2007/0269856 A1 | 11/2007 | Coffey | |
| 2008/0154031 A1 | 6/2008 | Berg et al. | |
| 2009/0325284 A1 | 12/2009 | Truran et al. | |
| 2010/0297177 A1 | 11/2010 | Buening et al. | |
| 2011/0243904 A1 * | 10/2011 | Cheng | A61P 31/18 424/93.21 |
| 2013/0052165 A1 | 2/2013 | Bangio et al. | |

FOREIGN PATENT DOCUMENTS

| | | |
|---|---|---|
| JP | 2011-524887 A | 9/2011 |
| JP | 2012-529917 A | 11/2012 |
| WO | 03/039459 A1 | 5/2003 |
| WO | 2009/153563 A1 | 12/2009 |
| WO | 2010/148143 A1 | 12/2010 |
| WO | WO 2010148143 * | 12/2010 |
| WO | 2011/086509 A1 | 7/2011 |
| WO | 2011/097447 A2 | 8/2011 |

OTHER PUBLICATIONS

Segura et al, New developments in lentiviral vector design, production and purification, Expert Opin. Biol. Ther. (2013) 13(7):987-1011.*
Millipore, Protein Concentration and Diafiltration by Tangential Flow Filtration, pp. 1-24, downloaded Jun. 22, 2020.*
Ansorge, et al., Recent progress in lentiviral vector mass production, Biochemical Engineering Journal, 2010, 48(3):362-377.
Benati, C., Production and purification of lentiviral vector for pre-clinical and clinical application, ASGCT/ESGCT Joint Clinical Trials Training, 2012, pp. 1-17.
Lesch, H.P., et al., Production and purification of lentiviral vectors generated in 293T suspension cells with baculoviral vectors, Gene Therapy, 2011, 18:531-538.
Zhou, et al., PEG-modulated column chromatography for purification of recombinant adeno-associated virus serotype 9, J. Virol. Methods, 2011, 173(1):99-107.
PCT International Application No. PCT/US14/30370, International Search Report dated Aug. 25, 2014.

* cited by examiner

*Primary Examiner* — Maria Marvich
(74) *Attorney, Agent, or Firm* — Pillsbury Winthrop Shaw Pittman LLP; Robert M. Bedgood

(57) ABSTRACT

Methods for preparing highly purified rLV vector formulations at the scale needed to meet anticipated demand for human gene therapy are provided.

38 Claims, 13 Drawing Sheets

SCALABLE MANUFACTURING PROCESS TO PRODUCE RECOMBINANT LENTIVIRAL VECTORS IN SERUM-FREE SUSPENSION CELL CULTURE SYSTEM

RELATED APPLICATION INFORMATION

This application is a continuation application of application Ser. No. 14/216,778, filed Mar. 17, 2014, now abandoned, which claims the benefit of priority to provisional application No. 61/787,818, filed Mar. 15, 2013, all of which applications are expressly incorporated herein by reference in their entirety.

FIELD OF THE INVENTION

This invention relates to the fields of molecular biology and gene therapy. More specifically, the invention provides improved processes for large scale production of viral vectors, preferably lentiviral and adeno-associated viral vectors, comprising transgenes which encode medically beneficial products for clinical use.

INTRODUCTION

Several publications and patent documents are cited throughout the specification in order to describe the state of the art to which this invention pertains. Each of these citations is incorporated herein by reference as though set forth in full.

Recombinant Lentivirus-based (rLenti) vectors have been developed and widely used as investigational gene delivery products for several serious human diseases. Lentiviral vectors have proven to be very productive in terms of transduction due to their ability to infect both replicating and non-replicating cells, including stem cells.

Many clinical trials have been initiated world-wide using HIV-1 based, VSVG pseudo-typed lentiviral vectors and very promising clinical benefits have been observed. However, a significant problem in the field at this time is a lack of methodology to make sufficient quantities of rLenti that will be need for advanced clinical studies. The research and clinical trial data have shown that rLentivector is a promising gene delivery vehicle for human gene therapy, for genetic diseases such as primary immunodeficiencies (Fischer and colleauges) as well as immunotherapeutics for cancers (June and colleagues).

However, there is a critical need in the field to develop scalable production and purification methods which are suitable for cGMP manufacture of large quantities of rLenti vectors which meet manufacturing capacity and investigational product quality requirements to support late stages of clinical applications. For example, for one very promising programs in Phase I for treatment of leukemias, it is anticipated that at least 100-fold greater manufacturing capacity relative the currently available methods will be required for Phase III studies and early stage licensed product launch. Thus, methods scaling up production of this gene therapy vector are urgently needed.

SUMMARY

In accordance with the invention, methods are provided for production of high titer rLenti vectors in a scalable, serum-free suspension cell culture and purification of the vector using scalable, industry standard column chromatography techniques. An rLV vector formulation comprising rLV particles produced according to the methods can be made, and optionally included in a pharmaceutically acceptable carrier.

In one embodiment, a method for viral vector purification includes: a) harvesting recombinant viral vectors comprising a transgene from serum free suspension culture; clarifying the harvest of step a) via filtration; c) harvesting the filtrate from step b) and optionally exposing said filtrate to nuclease digestion to remove DNA/RNA impurities; subjecting the filtrate of step c) to PEG-modulated affinity or ion exchange column chromatography, thereby isolating said viral vectors; further purifying the viral vectors obtained from step d) via tangential flow filtration to reduce the volume and buffer exchange; subjecting the filtrate of step e) to size exclusion column chromatography to further purify said viral vectors; subjecting the vectors of step f) to tangential flow filtration, and thereby obtaining final vector titer; filtering a vector solution obtained from step g) through a filter; and collecting said purified viral vectors.

In another embodiment, a method for viral vector purification includes: a) harvesting recombinant viral vectors comprising a transgene from serum free suspension culture; b) clarifying the harvest of step a) via filtration; c) subjecting the clarified suspension of step b) to tangential flow filtration to reduce volume and exchange buffer; d) harvesting the filtrate from step c) and optionally exposing said filtrate to nuclease digestion to remove DNA/RNA impurities; e) subjecting the filtrate of step d) to PEG-modulated affinity or ion exchange column chromatography, thereby isolating said viral vectors; f) subjecting the viral vectors obtained from step e) to size exclusion column chromatography to further purify said viral vectors; g) subjecting the vectors of step f) to tangential flow filtration, and thereby obtaining final vector titer; h) filtering a vector solution obtained from step g) through a filter; and i) collecting said purified viral vectors.

In a further embodiment, a method for viral vector purification includes: a) harvesting recombinant viral vectors comprising a transgene from serum free suspension culture; b) clarifying the harvest of step a) via filtration; c) subjecting the clarified suspension of step b) to tangential flow filtration to reduce volume and exchange buffer; d) harvesting the filtrate from step c) and optionally exposing said filtrate to nuclease digestion to remove DNA/RNA impurities; e) subjecting the filtrate of step d) to PEG-modulated affinity or ion exchange column chromatography, thereby isolating said viral vectors; f) further purifying the viral vectors obtained from step e) via tangential flow filtration to reduce the volume and buffer exchange; g) subjecting the filtrate of step f) to size exclusion column chromatography to further purify said viral vectors; h) subjecting the vectors of step g) to tangential flow filtration, and thereby obtaining final vector titer; filtering a vector solution obtained from step h) through a filter; and j) collecting said purified viral vectors.

Methods of the invention are applicable to lentiviral vectors (rLV). In particular embodiments, an rLV vector comprises a recombinant lentiviral vector (rLV) is an HIV-1, HIV-2, HIV-1/HIV-2 pseudotype, HIV-1/SIV, FIV, caprine arthritis encephalistis virus (CAEV), equine infectious anemia virus, bovine immunodeficiency virus, HIV and their pseudotypes, or a Vesucular Stomatitis Virus G-pseudotyped lentivirus (VSVG pseudotypede) vector.

Viral vectors in accordance with the invention include transgenes. In particular embodiments, a transgene encodes a nucleic acid selected from the group consisting of a siRNA, an antisense molecule, and a miRNA a ribozyme and a shRNA. In additional particular embodiments, a transgene encodes a gene product (protein or polypeptide).

In particular aspects, a gene product (protein or polypeptide) is insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor α (TGFα), platelet-derived growth factor (PDGF), insulin growth factors I and II (IGF-I and IGF-II), TGFβ, activins, inhibins, bone morphogenic protein (BMP), nerve growth factor (NGF), brain-derived neurotrophic factor (BDNF), neurotrophins NT-3 and NT4/5, ciliary neurotrophic factor (CNTF), glial cell line derived neurotrophic factor (GDNF), neurturin, agrin, netrin-1 and netrin-2, hepatocyte growth factor (HGF), ephrins, noggin, sonic hedgehog or tyrosine hydroxylase. In additional particular aspects, a gene product (protein or polypeptide) is thrombopoietin (TPO), interleukins (IL1 through IL-17), monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand, IgG, IgM, IgA, IgD and IgE, chimeric immunoglobulins, humanized antibodies, single chain antibodies, T cell receptors, chimeric T cell receptors, single chain T cell receptors, G protein-coupled receptors (GPCRs), CCR5, and class I and class II MHC molecules.

In further particular aspects, a gene product (protein or polypeptide) is a nucleic acid encoding a protein useful for correction of in born errors of metabolism selected from the group consisting of carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor V, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, retinal pigment epithelium-specific 65 kDa protein (RPE65), H-protein, T-protein, a cystic fibrosis transmembrane regulator (CFTR) sequence, or a dystrophin cDNA sequence. In still additional particular aspects, a gene product (protein or polypeptide) is Factor VIII or Factor IX.

In still further particular aspects, a transgene encodes a tumor associated antigen (TAA). In yet further particular aspects, a transgene encodes a gene product of any of CAIX, CD19, CD20, CD20, CD22, CD30, CD33, CD44v7/8, CEA, EGF-RIII (epidermal growth factor receptor variant 3) EGP-2, erb-B2, erb-B2, 3, 4, FBP, fetal acetycholine receptor, GD2, Her2/neu, IL-13R-a2, KDR, k-light chain, LeY, L1 cell adhesion molecule, MAGE-A1, mesothelin, MUC1, NKG2D, oncofetal antigen (h5T4), PSCA, PSMA, mAb IgE targeted TAA, TAG-72 or VEGF-R2.

Viral vectors in accordance with the invention may be produced by cells. In particular embodiments, recombinant viral vectors are produced by mammalian cells. In particular aspects, recombinant viral vectors are produced by HEK 293T (ATCC); HEK293F (Life Technologies); HEK293 (ATCC); 293S (ATCC), BHK (ATCC), BHK-21 (ATCC), CHO (ATCC), CHO/dhFr− (ATCC)1, or CHO K1 (ATCC) cells.

Cells producing recombinant viral vectors in accordance with the invention are typically grown in suspension in a growth medium. Growth medium for cells include serum free cell growth medium. In particular aspects, a serum free growth medium is FreeStyle™ 293 (Gibco®, Life Technologies), DMEM/F12 (Gibco®, Life Technologies), SFM4Transfx-293 (HyClone™, ThermoScientific), CDM4HEK293 (HyClone™, ThermoScientific), StemPro-34SFM (Gibco®, Life Technologies), FreeStyle F17 (Gibco®, Life Technologies), 293SFM II (Gibco®, Life Technologies), or CD293 (Gibco®, Life Technologies), or a combination thereof.

Nucleases can be employed in the invention methods. In particular embodiments, a nuclease is an endonuclease, an exonuclease, or a combination thereof. In additional particular embodiments, a nuclease is a deoxyribonuclease, a ribonuclease, or a combination thereof. In further particular embodiments, a nuclease is a benzonase or a DNase.

Various resins or chromatography substrates (media) can also be employed in the invention methods. In particular embodiments, affinity or ion exchange resin or substrate (media) can be employed. In particular aspects, ion exchange column chromatography comprises anion or cation exchange column chromatography, strong or weak anion exchange, or strong or weak cation exchange.

Methods of the invention also include additional steps of binding, washing and/or eluting in connection with column chromatography. Such binding, washing and/or eluting steps can be performed one or multiple times (e.g., 1, 2, 3, 4, 5, 6, 7, 8, 9, 10 times). In various embodiments, a method includes adjusting the filtrate of a prior step to be a binding solution (for binding of virus to the resin or media of the column); and/or contacting the filtrate with the affinity or ion exchange column thereby binding the viral vectors to the affinity or ion exchange column, and/or washing the bound viral vectors to remove impurities with a washing solution, the solution optionally including PEG or PEG and a salt; and/or eluting the viral vectors from the affinity or ion exchange column with an elution solution.

In particular aspects, a binding solution includes PEG in an amount from about 0% to 10% weight/volume, or from about 0% to 5% weight/volume, or from about 0% to 2% weight/volume. In additional particular aspects, a binding solution includes PEG having a molecular weight from about 2,000 kDa to about 40,000 kDa.

In particular aspects, a washing solution includes PEG in an amount from about 1% to 10% weight/volume, or from about 1% to 5% weight/volume, or from about 1% to 2% weight/volume. In additional particular aspects, a washing solution includes PEG having a molecular weight from about 2,000 kDa to about 40,000 kDa.

In particular aspects, an elution solution includes PEG in an amount from about 0% to 20% weight/volume. In additional particular aspects, an elution solution includes PEG having a molecular weight from about 2,000 kDa to about 40,000 kDa.

In invention methods, binding, washing and/or elution solutions can optionally include one or more salts. In particular embodiments, binding, washing and/or elution solution includes one or more salts in an amount from about 20 mM to about 1,000 mM (1M). Non-limiting salts include sodium chloride and/or potassium chloride.

In additional embodiments, a method for viral vector purification includes one or more filtering steps. In particular embodiments, filtering is through a filter having a pore diameter of about 0.20-0.5 um. In particular aspects, filtering is through a 0.20 um pore diameter filter, a 0.22 um pore diameter filter, or a 0.45 um pore diameter filter.

As disclosed herein, methods of the invention are able to produce high titers of purified viral vectors, for example, from $1\times10^5$ infectious units (IU)/ml viral vector, up to approximately $1\times10^9$ infectious units (IU)/ml viral vector. In particular embodiments, viral vector is produced at approximately $5\times10^5$ infectious units (IU)/ml, viral vector is produced at approximately $6\times10^6$ infectious units (IU)/ml, or viral vector is produced at approximately $3\times10^8$ infectious units (IU)/ml.

DETAILED DESCRIPTION

Figure 1A:
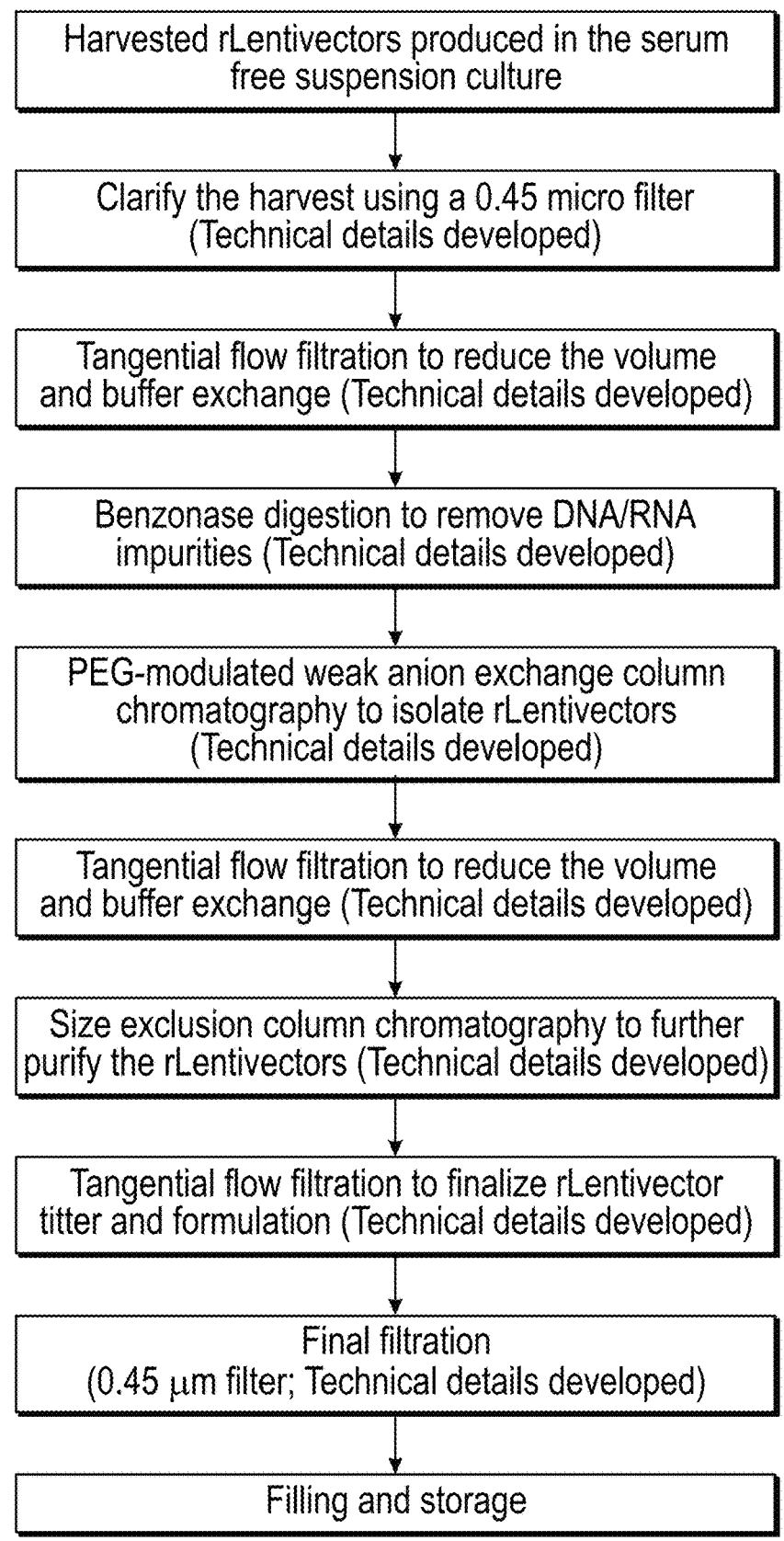
FIG. 1A-1D. Flow charts of exemplary methods for purification of lentiviral vectors of the invention.
Figure 1B:
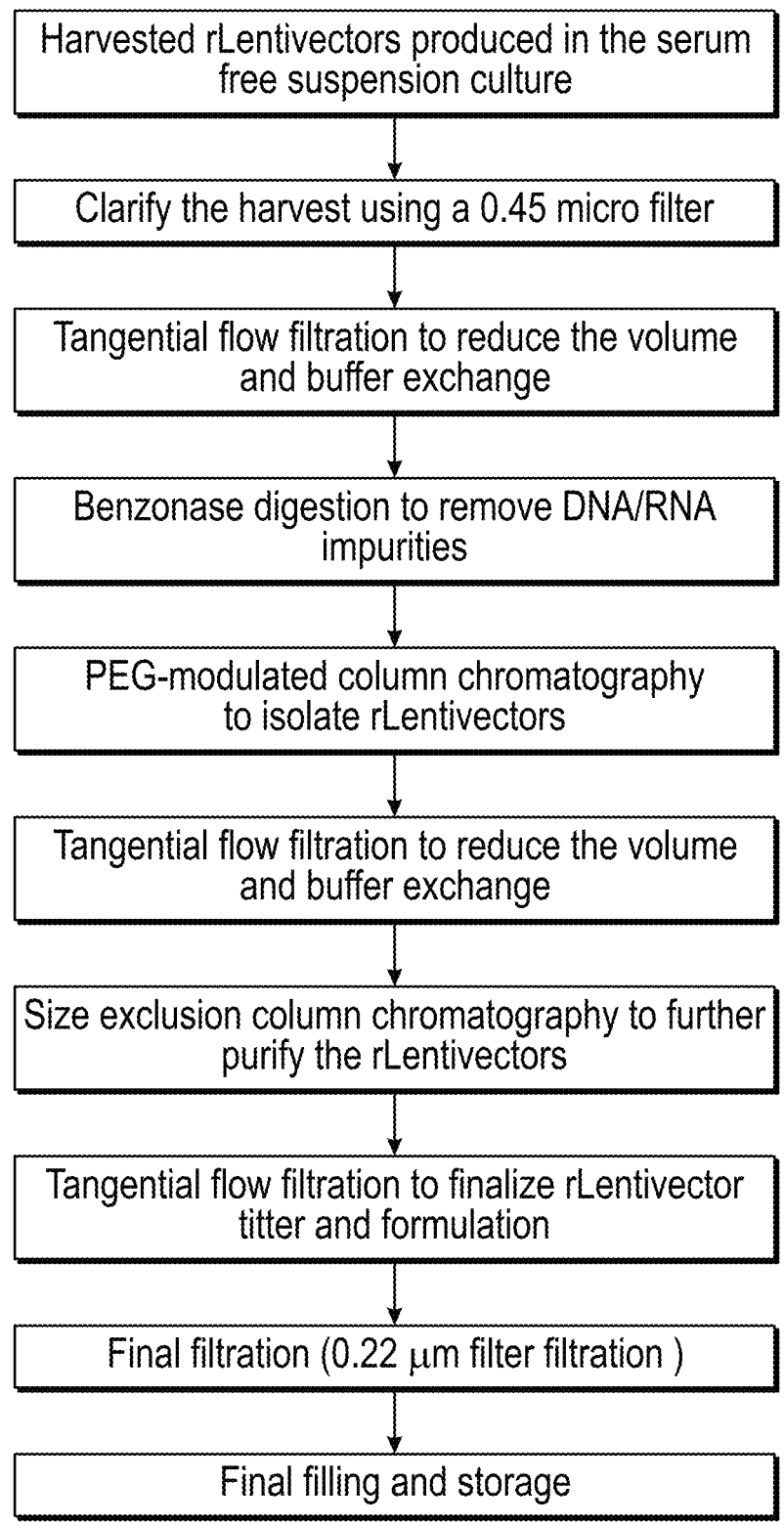
Figure 1C:
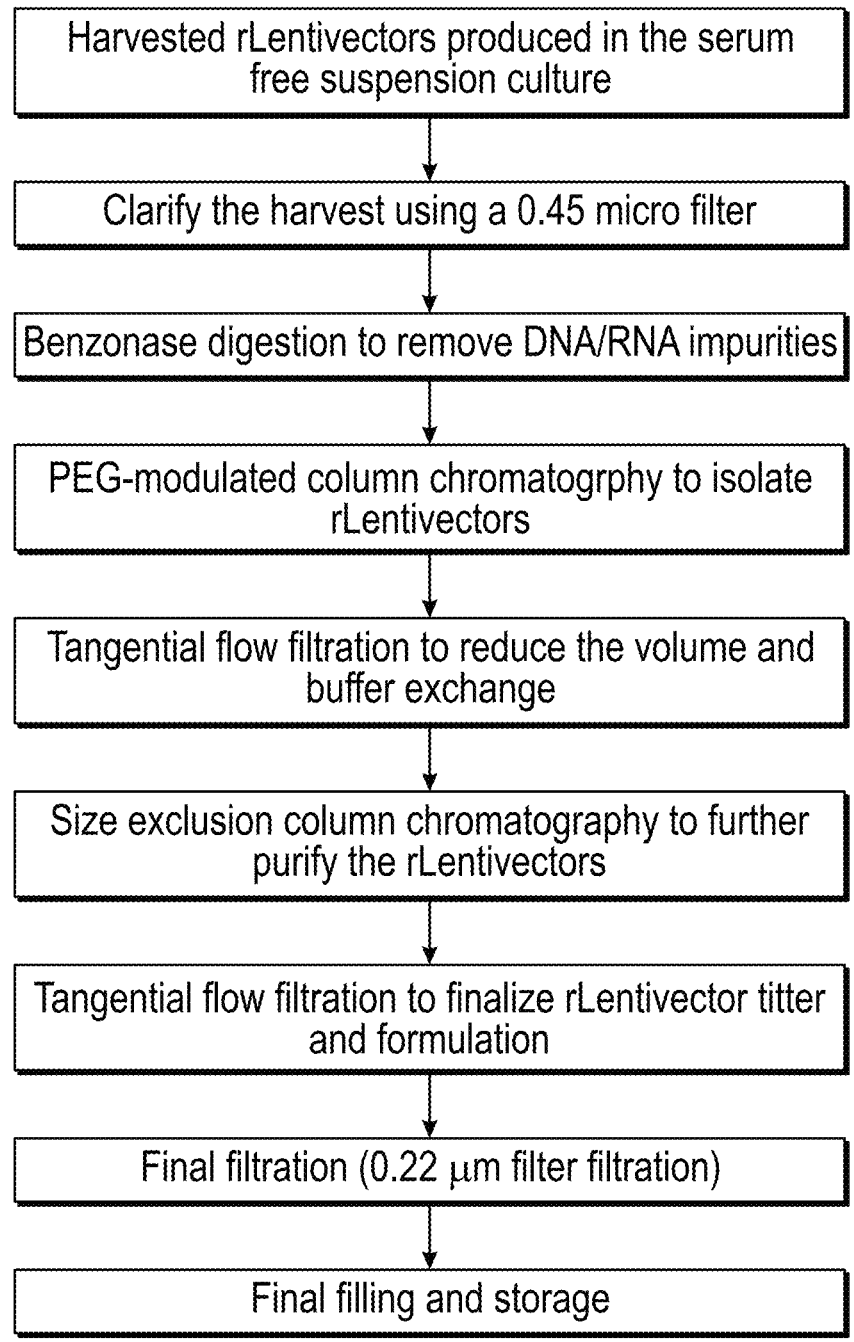
Figure 1D:
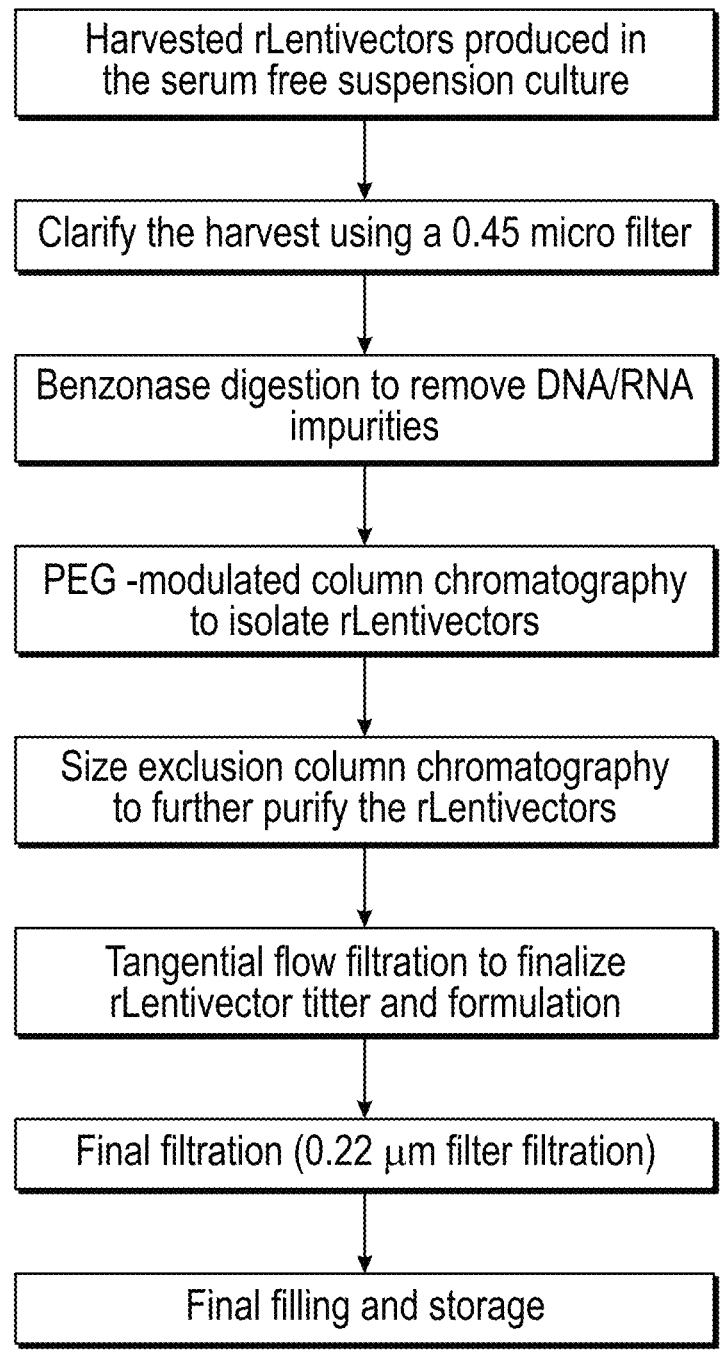

Recombinant Lentivirus vectors are typically produced by using transfection methods in research. There are several methods that are known in the art for generating rLV virions: for example, transfection using vector and rLV helper sequences (see for example, Merten et al 2011). However, when manufacturing rLenti vectors for clinical application, particularly for late stages of clinical applications, it is highly preferable to manufacture the vectors using a serum free suspension production system which can be scaled up to ensure the adequate manufacturing capacity and ensuring a superior safety profile of the vector manufactured.

Disclosed herein is a transfection-based production method to produce high titer of lentiviral vectors in a scalable serum free cell culture system. Cells from a commercial source, available as adapted for adherent growth, were successfully adapted into serum free cell culture media. We evaluated more than five different cell culture media which are claimed to support serum-free suspension cell culture, but identified only one media that support non-aggregated, healthy cell growth after adaption with fast growth rate. The adapted cells have been cultured in the serum free suspension culture condition for several months and a research cell bank has been developed.

Lentiviruses are enveloped viruses, and are significantly different in terms of virus structure and life cycle from other viruses used for delivery of nucleic acid into cells, such as adeno-associated viruses (AAV). Lentiviruses are composed of 2 copies of RNA, a nuclear capsid (NC), a Capsid (CA) a membrane associated matrix (MA), envelope proteins such as surface glycoproteins and transmembrane proteins and enzymes such as integrase (IN), protease (PR), reverse transcriptase (RT) and accessory proteins (e.g., Nef, Vif, Vpu, Vpr). Lentiviruses infect cells by binding of a surface glycoprotein of the virus to a receptor on the cell. The membranes of the envelope of the virus and the cell then fuse allowing the virus to enter the cell. Following entry, uncoating of viral RNA and reverse transcription takes place which leads to the formation of a pre-integration complex, which contains double stranded DNA, RT, IN, Vpr (or Vpx in HIV-2) NC, and some copies of the MA (Suzuki and Craigie 2007, Depienne et al., 2000, Bukrinsky et al., 1993 and Miller et al., 1997). Once the provirus enters the nuclear envelope, the viral DNA integrates within the cell genome. Normal cellular functions of transcription and translation are followed by assembly of structural viral proteins with viral RNA and subsequent viral budding.

Lentiviruses are desirable for delivery of nucleic acid into cells in part because they can infect non-dividing cells by actively entering the nucleus through the nuclear envelope. By contrast, other retroviruses require cell division for infection due to the fact that it cannot enter the nuclear envelope of a non-dividing cell.

"Lentiviruses" include members of the bovine lentivirus group, equine lentivirus group, feline lentivirus group, ovineecaprine lentivirus group and primate lentivirus group. Examples of lentiviruses suitable for the methods and use of the invention include, but are not limited to, HIV and their pseudotypes such as HIV-1, HIV-2, HIV-1/HIV-2 pseudotype, HIV-1/SIV, FIV, caprine arthritis encephalitis virus (CAEV), equine infectious anemia virus, bovine immunodeficiency virus and Vesucular Stomatitis Virus G-pseudotyped lentivirus (VSVG pseudotypede).

The development of lentiviral vectors for gene therapy has been reviewed in Klimatcheva et al., 1999, Frontiers in Bioscience 4: 481-496. The design and use of lentiviral vectors suitable for gene therapy is described, for example, in U.S. Pat. No. 6,207,455, issued Mar. 27, 2001, and U.S. Pat. No. 6,165,782, issued Dec. 26, 2000. Additional systems are disclosed in Merten et al. (2011).

The terms "gag polyprotein", "pol polyprotein", and "env polyprotein" refer to the multiple proteins encoded by retroviral gag, pol and env genes which are typically expressed as a single precursor "polyprotein". For example, HIV gag encodes, among other proteins, p17, p24, p9 and p6. HIV pol encodes, among other proteins, protease (PR), reverse transcriptase (RT) and integrase (IN). HIV env encodes, among other proteins, Vpu, gp120 and gp41. As used herein, the term "polyprotein" shall include all or any portion of gag, pol and env polyproteins.

The terms "Vpx" and "Vpr" refer respectively to lentiviral Vpx and Vpr proteins described, for example, in WO 96/07741, hereby incorporated by reference in its entirety. These terms also refer to fragments, mutants, homologs and variants of Vpr and Vpx which retain the ability to associate with p6.

The term "fusion protein" refers to a molecule comprising two or more proteins linked together. Typically, the fusion protein is an amino acid sequence comprising two or more protein sequences.

By "vector" is meant a genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

As used herein, the term "recombinant," as a modifier of sequences such as vector as well as a modifier of a virus, means that the compositions have been manipulated (i.e., engineered) in a fashion that generally does not occur in nature.

A "recombinant lentiviral vector" or "rLV" is a genetic element comprising a lentivirus linear, double-stranded nucleic acid genome. The lentivirus linear, double-stranded nucleic acid genome has been genetically altered, e.g., by the addition or insertion of a heterologous nucleic acid construct.

By "recombinant virus" is meant a virus that has been genetically altered, e.g., by the addition or insertion of a heterologous nucleic acid construct into the particle. A recombinant virus does not include infectious virus as they exist in nature.

A "LV virion" is meant a complete virus particle, such as a wild-type (wt) LV virus particle associated with an rLV envelope. By "rLV virion" is meant a complete virus particle, such as a rLV virus particle comprising a linear, double-stranded LV nucleic acid genome and a heterologous nucleotide sequence of interest associated with an rLV envelope. Examples of rLV suitable for the methods and uses of the invention include, but are not limited to, HIV and their pseudotypes such as HIV-1, HIV-2, HIV-1/HIV-2 pseudotype, HIV-1/SIV, FIV, caprine arthritis encephalitis virus (CAEV), equine infectious anemia virus, bovine immunodeficiency virus and Vesucular Stomatitis Virus G-pseudotyped lentivirus (VSVG pseudotyped).

The terms "recombinant rLV virion," "rLV vector particle," and "full particles" are defined herein as an infectious, replication-defective virus including an rLV membrane envelope, and a transgene comprising a heterologous nucleotide sequence of interest. A review describing rLV molecular features is provided in Dropulic (2011). As set forth herein, a "recombinant rLV virion" does not include infectious LV as they exist in nature.

The term "host cell" denotes, for example, microorganisms, yeast cells, insect cells, and mammalian cells, that can be, or have been, used as recipients of an rLV helper construct, an rLV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

An accessory function vector generally refers to a nucleic acid that includes a sequence providing an accessory or helper function. An accessory function vector can be transfected into a host cell, and the vector can provide or encode protein(s) that function to support rLV vector virion production in/by the host cell. An accessory function vector can be in the form of a plasmid, phage, transposon, cosmid, episome or integrated in the genome of the host cell.

The term "transfection" is used to refer to the uptake of foreign nucleic acid (e.g., DNA) by a cell, and a cell has been "transfected" when exogenous nucleic acid (e.g., DNA) has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties into suitable host cells.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

Cells and cell lines appropriate for serum free growth in suspension in accordance with the invention methods include mammalian cells. Exemplary non-limiting cells include, for example, HEK 293T (ATCC); HEK293F (Life Technologies); HEK293(ATCC); 293S (ATCC), BHK (ATCC), BHK-21 (ATCC), CHO (ATCC), CHO/dhFr− (ATCC)1, and CHO K1 (ATCC) cells.

Serum free cell growth medium for use in accordance with the invention methods are available commercially or can be made. Non-limiting exemplary serum free growth medium include, for example, FreeStyle™ 293 (Gibco®, Life Technologies), DMEM/F12 (Gibco®, Life Technologies), SFM4Transfx-293 (HyClone™, ThermoScientific), CDM4HEK293 (HyClone™, ThermoScientific), StemPro-34SFM (Gibco®, Life Technologies), FreeStyle F17 (Gibco®, Life Technologies), 293SFM II (Gibco®, Life Technologies), and CD293 (Gibco®, Life Technologies) media.

In the methods of the invention, a treatment or method step can be used to reduce or decrease the amount of a nucleic acid impurity. In particular embodiments, a nuclease is used to reduce or decrease the amount of a nucleic acid impurity in harvested or a preparation of recombinant viral vectors. In particular embodiments, a nuclease is an endonuclease, such as benzonase, an exonuclease, or a combination thereof. In particular embodiments, a nuclease is a deoxyribonuclease, a ribonuclease, or a combination thereof. In particular embodiments, a nuclease is a DNase.

In the methods of the invention, one or more column chromatography steps are performed. Various substrates are suitable as a resin or media (stationary phase) for column chromatography. Such resin or media (stationary phase) include charge based (ion exchange) or affinity resin or media.

In particular embodiments, ion exchange column chromatography is anion (strong or weak) exchange column chromatography, or cation (strong or weak) exchange column chromatography. In more particular embodiments, an ion exchange column is a quarternized polyehtyleneimine based resin or media; or a quaternary amine based resin or media. In further more particular embodiments, an ion exchange column is a polyethyleneimine based resin; a Diethylaminoethyl (DEAE) based resin; or a Diethylaminopropyl based resin.

In particular embodiments, an affinity column is a Sulphopropyl based resin or media, or a carboxymethyl based resin or media. In additional particular embodiments, an affinity column is a multifunctional chromatography resin or media; a Metal Chelate Affinity resin or media; a heparin based resin or media, or a group specific affinity resin or media.

Additional resins or media suitable for column chromatography in the methods of the invention include an Hydroxyapatite (($Ca_5(PO_4)_3OH$)$_2$) based resin or media; a multimodal weak cation exchange resin or media; N-benzyl-n-methyletheanolamine based resin or media; or an Octylamine based resin or media.

In the methods of the invention, solutions are used, such as binding, washing and eluting solutions. The terms are used for convenience to refer to the purpose of the solution within the context of chromatography.

Such solutions can optionally include ingredients such as polyethylene glycol (PEG). Such solutions also can optionally include ingredients such as salts. In addition, such solutions can optionally include ingredients such as buffering agents (tris- or phosphate-buffered). Furthermore, such solutions can include ingredients such as chelating agents, for example, EDTA.

In particular embodiments, the amount of PEG in a binding solution is from about 0% to 10% weight/volume, or from about 0% to 5% weight/volume, or from about 0% to 2% weight/volume. In particular embodiments, the amount of PEG in a washing solution is from about 1% to 10% weight/volume, or from about 1% to 5% weight/volume, or from about 1% to 2% weight/volume. In particular embodiments, the amount of PEG in an elution solution is from about 0% to 20% weight/volume.

In particular embodiments, PEG in a binding, washing or eluting solution has a molecular weight from about 2,000 kDa to about 40,000 kDa. In other particular embodiments, PEG in a binding, washing or eluting solution has a molecular weight from about 2,000 kDa to about 10,000 kDa In particular embodiments, a salt comprises or consists of sodium chloride (NaCl), potassium chloride (KCl), or calcium chloride. In particular embodiments, the amount of a salt in a binding, washing or eluting solution is from about 20 mM to about 1 M. In more particular embodiments, the amount of a salt in a binding solution, is from about 20 mM to about 200 mM (such as about 100 mM). In more particular embodiments, the amount of a salt in a washing solution, is from about 20 mM to about 200 mM (such as 100 mM). In more particular embodiments, the amount of a salt in an eluting solution is from about 200 mM to about 1 M (such as 200 mM, 250 mM, 300 mM, 350 mM, 400 mM, 450 mM, or 500 mM) or from about 500-1,000 mM, or 600-800 mM.

In the methods of the invention, filters may be employed. Filters can be of various pore size diameters. The pore size diameter can conveniently be represented by a numerical value. Exemplary pore sizes range from about 0.20-0.5 um (micron). Additional exemplary pore sizes range from about 0.20 um (micron) to about 0.22 um (micron), or more particularly about 0.22 um (micron). Further exemplary pore sizes range from about 0.22 um (micron) to about 0.30 um (micron), or about 0.30 um (micron) to about 0.45 um (micron) pore diameter, or more particularly about 0.45 um (micron).

The invention methods provide an increase in rLV titers during large scale production while reducing, decreasing or eliminating, rLV vector related impurities (e.g. rLV associated nucleic acid impurities) contained within purified stocks of rLV virions, with minimal loss to rLV vector particles or virions contained therein. Impurities include protein, nucleic acid (DNA, RNA), debris, and other material distinct from rLV vector particles or virions that may be present. Invention methods serve to increase the amount of rLV vector particles/virions while reducing decreasing or eliminating impurities.

In particular embodiments, a method of the invention results in viral vector produced at approximately $5\times10^5$ infectious units (IU)/ml, or more. In particular embodiments, a method of the invention results in viral vector produced at approximately $6\times10^6$ infectious units (IU)/ml, or more. In particular embodiments, a method of the invention results in viral vector produced at approximately $3\times10^8$ infectious units (IU)/ml.

As used herein, the term "about" or "approximately" when used in reference to a quantity or unit measure refers to a range of statistical deviation acceptable for the represented numerical values. Typically, the range is about +/−10%, or +/−5% of the represented numerical value.

As disclosed herein, a recombinant (viral) vector may include a nucleic acid, such as a transgene. A "nucleic acid" sequence refers to a DNA or RNA sequence. The term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil-, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, Buracil-5-oxyacetic acid methylester, uracil-5-oxyacetic acid, pseudouracil, queosine, 2-thiocytosine, and 2,6-diaminopurine.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters."

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to as is conventional in the art.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "therapeutic molecule" in one embodiment is a peptide or protein that may alleviate or reduce symptoms that result from an absence or defect in a protein in a cell or subject. Alternatively, a "therapeutic" peptide or protein encoded by a transgene is one that confers a benefit to a subject, e.g., to correct a genetic defect, to correct a gene (expression or functional) deficiency, or an anti-cancer effect. Accordingly, a transgene comprising the heterologous nucleic acid can encode a number of useful products. These can include siRNA, antisense molecules, and miRNAs for example.

Transgenes can encode hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor α (TGFα), platelet-derived growth factor (PDGF), insulin growth factors I and II (IGF-I and IGF-II), any one of the transforming growth factor β superfamily, including TGFβ, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-17, monocyte chemoattractant protein, leukemia inhibitory factor, granulocyte-macrophage colony stimulating factor, Fas ligand, tumor necrosis factors α and β, interferons α, β, and γ, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors single chain T cell receptors (e.g. Kalos et al 2011; Porter et al 2011), G protein-coupled receptors (GPCRs) such as CCR5, class I and class II MHC molecules, as well as engineered immunoglobulins and MHC molecules. Useful gene products also include regulatory proteins such as complement regulatory proteins, membrane cofactor protein (MCP), decay accelerating factor (DAF), CR1, CF2 and CD59.

Other useful gene products include those that can correct in born errors of metabolism. Such transgenes can encode for example, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, blood clotting factors such as Factor V, Factor VIIa, Factor VIII, Factor IX, Factor X, Factor XIII, or protein C, cystathione beta-synthase, branched chain ketoacid decarboxylase, albumin, isovalerylcoA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence.

Further useful gene products include those that can provide for a defective, deficient or missing function or activity, for example, an antibody, retinal pigment epithelium-specific 65 kDa protein (RPE65), erythropoietin, LDL receptor, lipoprotein lipase, ornithine transcarbamylase, β-globin, α-globin, spectrin, α-antitrypsin, adenosine deaminase (ADA), a metal transporter (ATP7A or ATP7), sulfamidase, an enzyme involved in lysosomal storage disease (ARSA), hypoxanthine guanine phosphoribosyl transferase, β-25 glucocerebrosidase, sphingomyelinase, lysosomal hexosaminidase, branched-chain keto acid dehydrogenase, a hormone, a growth factor (e.g., insulin-like growth factors 1 and 2, platelet derived growth factor, epidermal growth factor, nerve growth factor, neurotrophic factor −3 and −4, brain-derived neurotrophic factor, glial derived growth factor, transforming growth factor α and β, etc.), a cytokine (e.g., α-interferon, β-interferon, interferon-γ, interleukin-2, interleukin-4, interleukin 12, granulocyte-macrophage colony stimulating factor, lymphotoxin, etc.), a suicide gene product (e.g., herpes simplex virus thymidine kinase, cytosine deaminase, diphtheria toxin, cytochrome P450, deoxycytidine kinase, tumor necrosis factor, etc.), a drug resistance protein (e.g, that provides resistance to a drug used in cancer therapy), a tumor suppressor protein (e.g., p53, Rb, Wt-1, NF1, Von Hippel-Lindau (VHL), adenomatous polyposis coli (APC)), a peptide with immunomodulatory properties, a tolerogenic or immunogenic peptide or protein Tregitopes, or hCDR1, insulin, glucokinase, guanylate cyclase 2D (LCA-GUCY2D), Rab escort protein 1 (Choroideremia), LCA 5 (LCA-Lebercilin), ornithine ketoacid aminotransferase (Gyrate Atrophy), Retinoschisin 1 (X-linked Retinoschisis), USH1C (Usher's Syndrome 1C), X-linked retinitis pigmentosa GTPase (XLRP), MERTK (AR forms of RP: retinitis pigmentosa), DFNB1 (Connexin 26 deafness), ACHM 2, 3 and 4 (Achromatopsia), PKD-1 or PKD-2 (Polycystic kidney disease), TPP1, CLN2, gene deficiencies causative of lysosomal storage diseases (e.g., sulfatases, N-acetylglucosamine-1-phosphate transferase, cathepsin A, GM2-AP, NPC1, VPC2, Sphingolipid activator proteins, etc.), one or more zinc finger nucleases for genome editing, or donor sequences used as repair templates for genome editing.

Transgenes also can encode a tumor associated antigens (TAAs). Non-limiting TAAs include: tumor-associated testis-specific antigen (e.g., MAGE, BAGE, and GAGE), melanocyte differentiation antigen (e.g., tyrosinase, Melan-A/MART-1), CDK4, MUM-1, beta-catenin, gp100/pmel 17, TRP-1, TRP-2, an MITF, MITF-A and MITF-M (King, et al. (1999). Am J Pathol 155:731). Additional non-limiting examples of TAAs expressed by tumors include melanoma GP75, Annexin I, Annexin II, adenosine deaminase-binding protein (ADAbp), PGP 9.5 (Rode, et al. (1985). Histopathology 9:147), colorectal associated antigen (CRC)—0017-1A/GA733, Ab2 BR3E4, CI17-1A/GA733, Hsp70 (Chen, et al. (2002). Immunol Lett 84:81), Hsp90, Hsp96, Hsp105, Hsp110, HSPPC-96 (Caudill, M. M. and Z. Li (2001). Expert Opin Biol Ther 1:539), stress protein gp96 (Heike et al. (2000). Int J Can 86:489), gp96-associated cellular peptides, G250, Dipeptidyl peptidase IV (DPPIV), Mammaglobin (Tanaka, et al. (2003). Surgery 133:74), thyroglobulin, STn (Morse, M. A. (2000). Curr Opin Mol Ther 2:453), Carcinoembryonic Antigen (CEA), Carcinoembryonic Antigen (CEA) epitope CAP-1, Carcinoembryonic Antigen (CEA) epitope CAP-2, etv6, aml1, Prostate Specific Antigen (PSA), PSA epitopes PSA-1, PSA-2, PSA-3 (Correale, et al. (1998). J Immunol 161:3186), Ad5-PSA, Parathyroid-hormone-related protein (PTH-rP), EGFR (Plunkett, et al. (2001). J Mammary Gland Biol Neoplasia 6:467), PLU1 (Plunkett, et al. (2001). J Mammary Gland Biol Neoplasia 6:467), Oncofetal antigen-immature laminin receptor (OFA-iLR), MN/CA IX (CA9) (Shimizu et al., (2003). Oncol. Rep. September-October; 10:1307), HP59, Cytochrome oxidase 1, sp100, msa (Devine, et al. (1991). Cancer Res 51:5826), Ran GTPase activating protein, a Rab-GAP (Rab GTPase-activating) protein, PARIS-1 (Zhou, et al. (2002). Biochem Biophys Res Commun 290:830), T-cell receptor/CD3-zeta chain, cTAGE-1, SCP-1, Glycolipid antigen-GM2, GD2 or GD3, GM3 (Bada, et al. (2002). Hum Exp Toxicol 21:263), FucosylGM1, Glycoprotein (mucin) antigens-Tn, Sialyl-Tn (Lundin, et al. (1999). Oncology 57:70), TF and Mucin-1 (Mukherjee, et al. (2003). J Immunother 26:47), CA125 (MUC-16) (Reinartz, et al. (2003). Cancer Res 63:3234), a MAGE family antigen, GAGE-1,2, BAGE, RAGE, LAGE-1 (Eichmuller, et al. (2003). Int J Cancer 104:482) (Chen, et al. (1998). Proc Natl Acad Sci USA 95:6919), GnT-V (Murata, et al. (2001). Dis Colon Rectum 44:A2-A4), MUM-1 (Kawakami, et al. (1996). Keio J Med 45:100), EP-CAM/KSA (Ullenhag, et al. (2003). Clin Cancer Res 9:2447), CDK4, a MUC family antigen, HER2/neu, ErbB-2/neu, p21ras, RCAS1, α-fetoprotein, E-cadherin, α-catenin, β-catenin and γ-catenin, NeuGcGM3 (Carr, et al. (2003). J Clin Oncol 21:1015), Fos related antigen (Luo, et al. (2003). Proc Natl Acad Sci USA 100:8850), Cyclophilin B (Tamura, et al. (2001). Jpn J Cancer Res 92:762), RCAS1, S2 (Koga, et al. (2003). Tissue Antigens 61:136), L10a (Koga, et al. (2003). supra), L10a, Telomerase rt peptide (Wang, et al. (2001). Oncogene 20:7699), cdc27, fodrin, p120ctn, PRAME, GA733/EoCam (Ross, et al. (1986). Biochem Biophys Res Commun 135:297), NY-BR-1, NY-BR-2 NY-BR-3, NY-BR-4 NY-BR-5, NY-BR-6 NY-BR-7 (Jager, et al. (2001). Cancer Res 61:2055), NY-ESO-1, L19H1, MAZ (Daheron, et al. (1998). Leukemia 12:326), PINCH (Greiner, et al. (2000). Exp Hematol 28:1413), PRAME (Ikeda, et al. (1997) Immunity 6:199), Prplp/Zerlp, WT1 (Oka, et al. (2002). Curr Cancer Drug Targets 2:45), adenomatous polyposis coli protein (APC), PHF3, LAGE-1, SART3 (Miyagi, et al. (2001). Clin Cancer Res 7:3950), SCP-1 (Jager, et al. (2002). Cancer Immun 2:5), SSX-1, SSX-2, SSX-4, TAG-72 (Buchsbaum, et al. (1999). Clin Cancer Res 5(10 Suppl): 3048s-3055s), TRAG-3 (Chen, et al. (2002). Lung Cancer 38:101), MBTAA (Basu, et al. (2003). Int J Cancer 105: 377), a Smad tumor antigen, lmp-1, HPV-16 E7, c-erbB-2, EBV-encoded nuclear antigen (EBNA)-1, Herpes simplex thymidine kinase (HSVtk), alternatively spliced isoform of XAGE-1 (L552S; Wang, (2001). Oncogene 20:7699), TGF beta RII frame shift mutation (Saeterdal, et al. (2001). Proc Natl Acad Sci USA 98:13255), BAX frame shift mutation (Saeterdal, et al. (2001). Proc Natl Acad Sci USA 98:13255).

Transgenes additionally can encode a gene product, such as CAIX, CD19, CD20, CD20, CD22, CD30, CD33, CD44v7/8, CEA, EGF-RIII (epidermal growth factor receptor variant 3) EGP-2, erb-B2, erb-B2, 3, 4, FBP, fetal acetycholine receptor, GD2, Her2/neu, IL-13R-a2, KDR, k-light chain, LeY, L1 cell adhesion molecule, MAGE-A1, mesothelin, MUC1, NKG2D, oncofetal antigen (h5T4), PSCA, prostate-specific membrane antigen (PSMA), Prostatic Acid Phosphatase (PAP), Prostate epithelium-derived Ets transcription factor (PDEF), mAb IgE targeted TAA, TAG-72 and VEGF-R2.

Alternatively, transgenes can include siRNA, antisense molecules, and miRNAs for example. Clinically useful lentiviral vectors may also express an antisense gene directed against the human immunodeficiency virus (HIV) (Levine et al 2006) and other important human pathogens. These and other useful applications of rLV and related vectors have been recently reviewed and cited by Naldini (2011).

Antisense genes that can be included in an rLV vector can inhibit expression of: huntingtin (HTT) gene, a gene associated with dentatorubropallidolusyan atropy (e.g., atrophin 1, ATN1); androgen receptor on the X chromosome in spinobulbar muscular atrophy, human Ataxin-1, -2, -3, and -7, $Ca_v2.1$ P/Q voltage-dependent calcium channel is encoded by the (CACNA1A), TATA-binding protein, Ataxin 8 opposite strand, also known as ATXN8OS, Serine/threonine-protein phosphatase 2A 55 kDa regulatory subunit B beta isoform in spinocerebellar ataxia (type 1, 2, 3, 6, 7, 8, 12 17), FMR1 (fragile X mental retardation 1) in fragile X syndrome, FMR1 (fragile X mental retardation 1) in fragile X-associated tremor/ataxia syndrome, FMR1 (fragile X mental retardation 2) or AF4/FMR2 family member 2 in fragile XE mental retardation; Myotonin-protein kinase (MT-PK) in myotonic dystrophy; Frataxin in Friedreich's ataxia; a mutant of superoxide dismutase 1 (SOD1) gene in amyotrophic lateral sclerosis; a gene involved in pathogenesis of Parkinson's disease and/or Alzheimer's disease; apolipoprotein B (APOB) and proprotein convertase subtilisin/kexin type 9 (PCSK9), hypercoloesterolemia; HIV Tat, human immunodeficiency virus transactivator of transcription gene, in HIV infection; HIV TAR, HIV TAR, human immunodeficiency virus transactivator response element gene, in HIV infection; C—C chemokine receptor (CCR5) in HIV infection; Rous sarcoma virus (RSV) nucleocapsid protein in RSV infection, liver-specific microRNA (miR-122) in hepatitis C virus infection; p53, acute kidney injury or delayed graft function kidney transplant or kidney injury acute renal failure; protein kinase N3 (PKN3) in advance recurrent or metastatic solid malignancies; LMP2, LMP2 also known as proteasome subunit beta-type 9 (PSMB 9), metastatic melanoma; LMP7, also known as proteasome subunit beta-type 8 (PSMB 8), metastatic melanoma; MECL1 also known as proteasome subunit beta-type 10 (PSMB 10), metastatic melanoma; vascular endothelial growth factor (VEGF) in solid tumors; kinesin spindle protein in solid tumors, apoptosis suppressor B-cell CLL/lymphoma (BCL-2) in chronic myeloid leukemia; ribonucleotide reductase M2 (RRM2) in solid tumors; Furin in solid tumors; polo-like kinase 1 (PLK1) in liver tumors, diacylglycerol acyltransferase 1 (DGAT1) in hepatitis C infection, beta-catenin in familial adenomatous polyposis; beta2 adrenergic receptor, glaucoma; RTP801/Reddl also known as DAN damage-inducible transcript 4 protein, in diabetic macular oedma (DME) or age-related macular degeneration; vascular endothelial growth factor receptor I (VEGFR1) in age-related macular degeneration or choroidal neivascularization, caspase 2 in non-arteritic ischaemic optic neuropathy; Keratin 6A N17K mutant protein in pachyonychia congenital; influenza A virus genome/gene sequences in influenza infection; severe acute respiratory syndrome (SARS) coronavirus genome/gene sequences in SARS infection; respiratory syncytial virus genome/gene sequences in respiratory syncytial virus infection; Ebola filovirus genome/gene sequence in Ebola infection; hepatitis B and C virus genome/gene sequences in hepatitis B and C infection; herpes simplex virus (HSV) genome/gene sequences in HSV infection, coxsackievirus B3 genome/gene sequences in coxsackievirus B3 infection; silencing of a pathogenic allele of a gene (allele-specific silencing) like torsin A (TOR1A) in primary dystonia, pan-class I and HLA-allele specific in transplant; mutant rhodopsin gene (RHO) in autosomal dominantly inherited retinitis pigmentosa (adRP); or the inhibitory nucleic acid binds to a transcript of any of the foregoing genes or sequences.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations disclosed herein are incorporated by reference in their entirety. In case of conflict, the specification, including definitions, will control.

All of the features disclosed herein may be combined in any combination. Each feature disclosed in the specification may be replaced by an alternative feature serving a same, equivalent, or similar purpose. Thus, unless expressly stated otherwise, disclosed features (e.g., a recombinant vector (e.g., rLV) vector, or recombinant virus particle are an example of a genus of equivalent or similar features.

As used herein, the singular forms "a", "and," and "the" include plural referents unless the context clearly indicates otherwise. Thus, for example, reference to "a polynucleotide" includes a plurality of such polynucleotides, reference to "a vector" includes a plurality of such vectors, and reference to "a virus" or "particle" includes a plurality of such virions/particles.

As used herein, all numerical values or numerical ranges include integers within such ranges and fractions of the values or the integers within ranges unless the context clearly indicates otherwise. Thus, to illustrate, reference to at least 1-10%% identity, includes 1%, 2%, 3%, 4%, 5%, 6%, 7%, 8%, 9%, 10%, as well as 1.1%, 1.2%, 1.3% 1.4%, 1.5%, etc., 2.1%, 2.2%, 2.3%, 2.4%, 2.5%, etc., and so forth.

Reference to a number with more (greater) or less than includes any number greater or less than the reference number, respectively. Thus, for example, a reference to less than 40,000, includes 39,999, 39,998, 39,997, etc. all the way down to the number one (1); and less than 100, includes 99, 98, 97, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 2,000-40,000 includes 2,000; 3,000; 4,000; 5,000, 6,000, etc. as well as 2,100; 3,100; 4,100; 5,100; 6,100; etc., and so forth. Reference to a range of 20-100 therefore includes 21, 22, 23, 24, 25, 26, 27, 28, 29, 30, 31, 32, 33, 34, 35, 36, 37, 38, 39, 40, etc., up to and including 100, as well as 21.1, 21.2, 21.3, 21.4, 21.5, etc., 22.1, 22.2, 22.3, 22.4, 22.5, etc., and so forth.

Reference to a series of ranges includes ranges which combine the values of the boundaries of different ranges within the series. Thus, to illustrate reference to a series of ranges of 20-100 or 100-1,000 (e.g., 20 mM-100 mM; or 100 mM-1M) includes 20-30, 30-40, 40-50, 50-60, 60-75, 75-100, 100-150, 150-200, 200-250, 250-300, 300-400, 400-500, 500-750, 750-1,000, etc.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. Accordingly, the following examples are intended to illustrate but not limit the scope of the invention claimed.

EXAMPLES

Example 1

Lentivirus vectors are typically produced by transfection methods using calcium phosphate precipitation method in adherent cell culture system (3, 4). However, when manufacturing lentivectors for clinical application, particularly for late stages of clinical applications, it is critical to manufacture the vectors in a serum free suspension production system which can be scaled up to ensure the quantity of the vector production and enhance the safety profile of the vector manufactured.

Figure 2A:
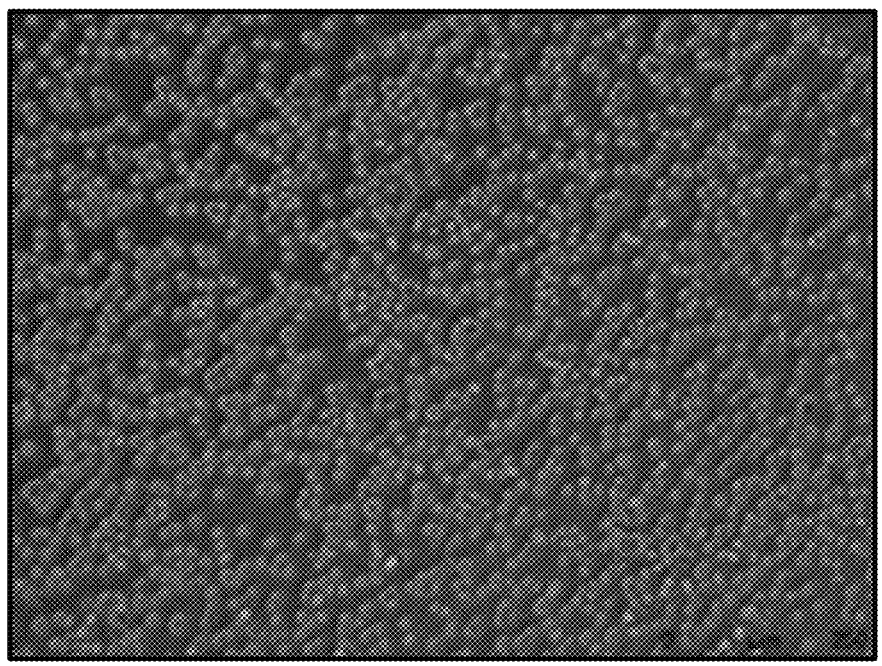
FIG. 2A-2C. Characterization of adapted HEK 293T cell growth in serum free suspension culture. A: Light microscope image depicting cell population adapted in CD293 serum free media, no cell aggregation observed. B. Optimization of cell culture conditions using spinner flasks. Under the condition of 8% CO2 and 130 rotation per min, the cells can be cultured for four days and about 3E+06 cells per ml. C. Cell growth rate is consistent with doubling time about 20 hours.
Figure 2B:
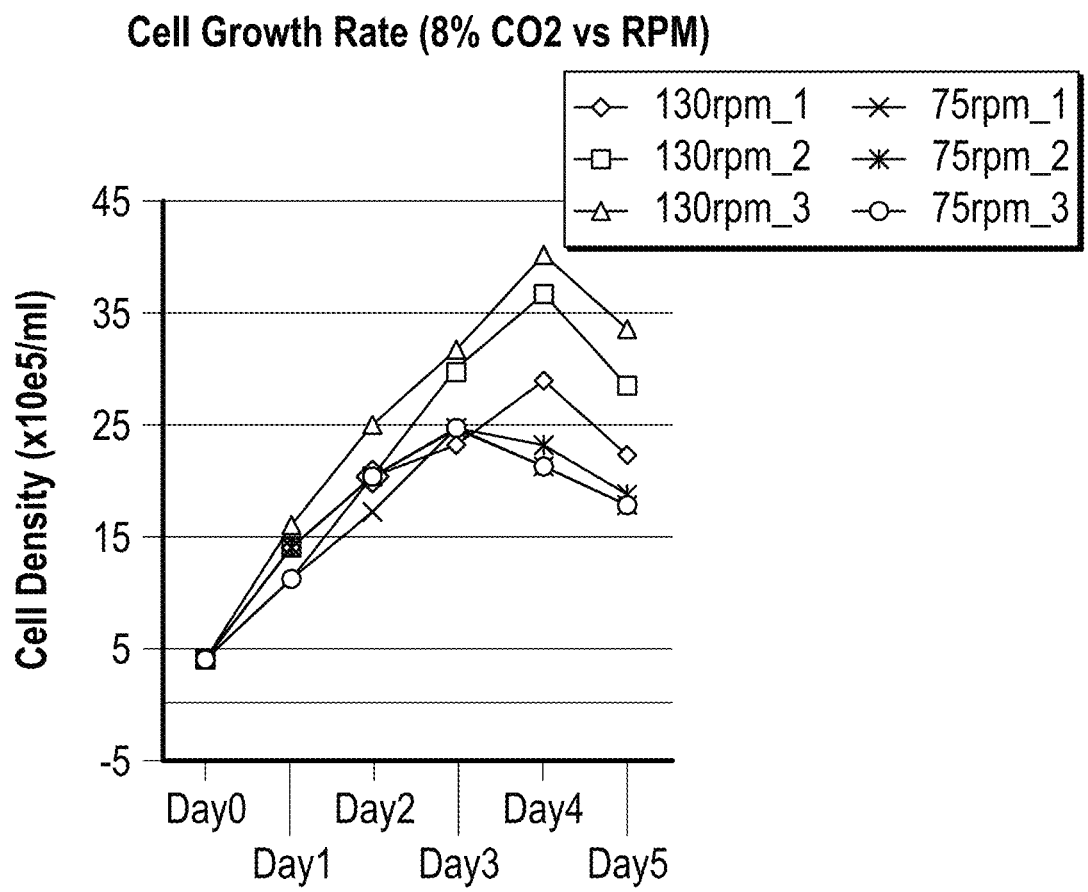
Figure 2C:
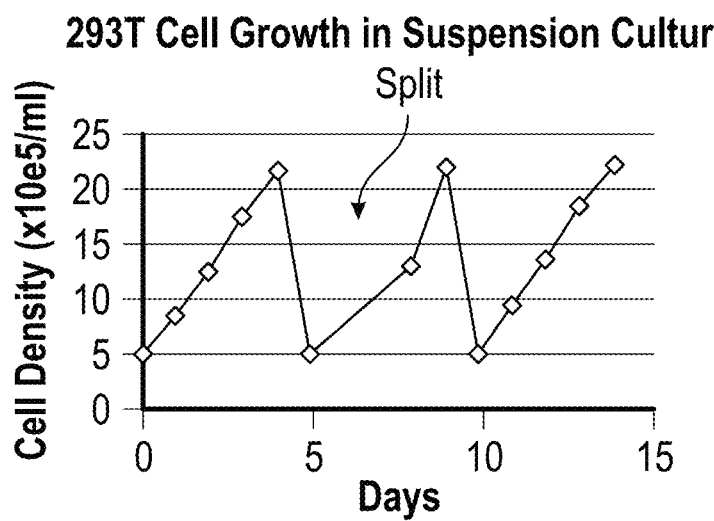
Figure 3A:
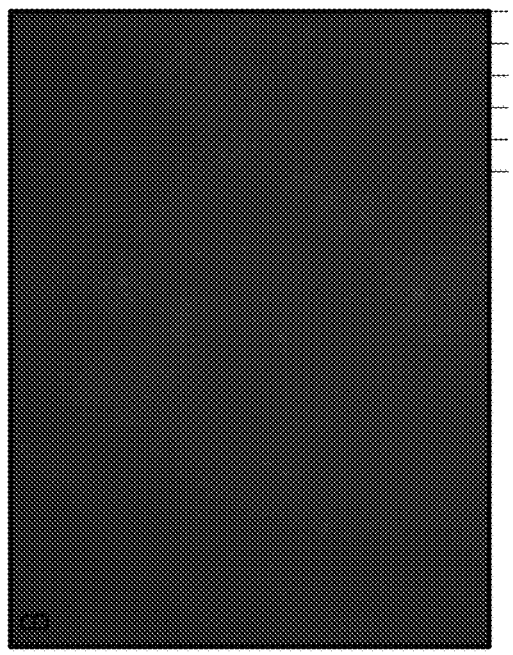
FIG. 3A-3D. Fluorescent microscope images depicting eGFP expression in PEI transfected HEK 293 T cells in serum free suspension culture. Panel A, B, C and D are cells in different serum free culture media. eGFP positive cells are detected only in Panel D.
Figure 3B:
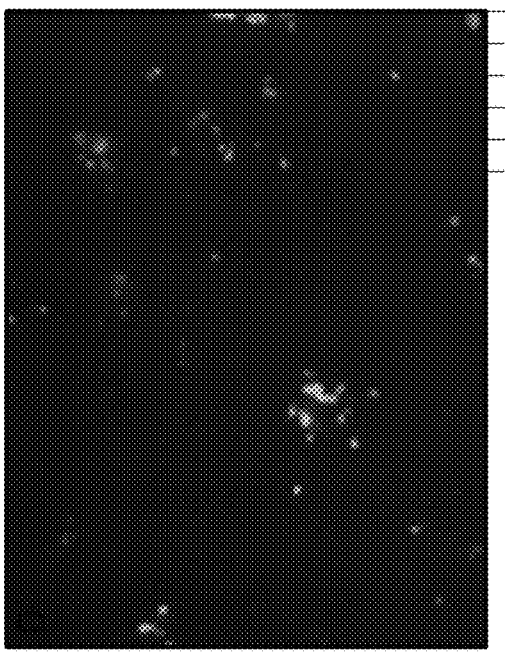
Figure 3C:
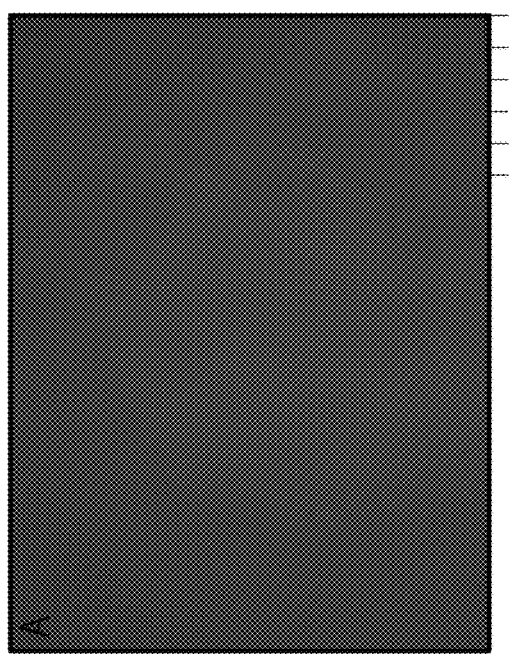
Figure 3D:
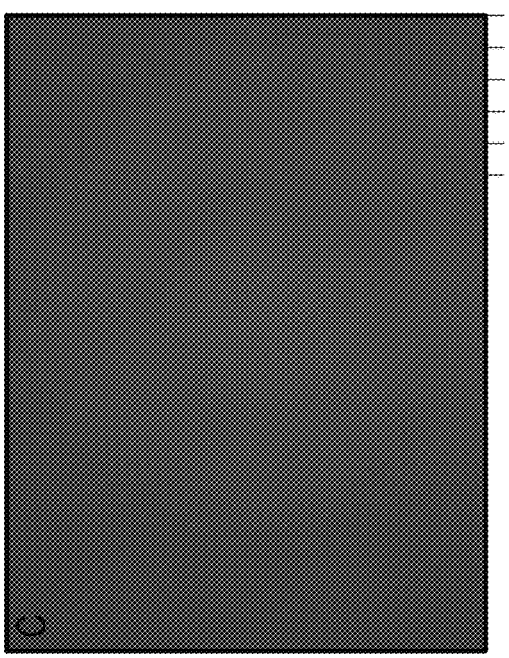

To overcome the existing limitations of currently available Lentivector production systems, disclosed herein is a scalable serum free, suspension cell culture system producing high titer lentivectors. The first step in this new scalable production system is the development of a cell line that can be cultured in serum free condition and produces high levels of lentivectors. We hypothesized that adapting HEK293T cells to serum free suspension culture should be feasible as these cells are currently widely used in producing viral vectors. To achieve this goal, we designed a step wise adaption protocol and systemically evaluated several commercially available serum-free cell culture media and the ability of HEK 293T cells to grow robustly in these media. One media (CD293) was found to outperform all of the others tested in supporting non-aggregated, healthy cell growth after adaption with fast growth rate (FIG. 2, Panel A). The optimized cell culture condition support high cell density and consistent cell growth (FIG. 2, Panel B and C). The adapted cells have been cultured under serum free suspension culture conditions for several months, and a research cell bank has been developed.

Lentiviral vectors have been produced by calcium phosphate precipitation co-transfection of 2 to 5 plasmids into target cells. While the latest generation of the multiplasmid production system (self in activation system) has been shown to be versatile in producing lentivectors with a reduced risk of generating replication competent lentivirus, the calcium co-precipitation imposes a limitation on large-scale manufacture. Calcium phosphate co-precipitation of DNA, developed over 40 years ago (5), works well for adherent cell culture in research scale. However, it does not provide efficient levels of transfection in serum free suspension cell cultures and is very difficult to scale up.

Figure 4:
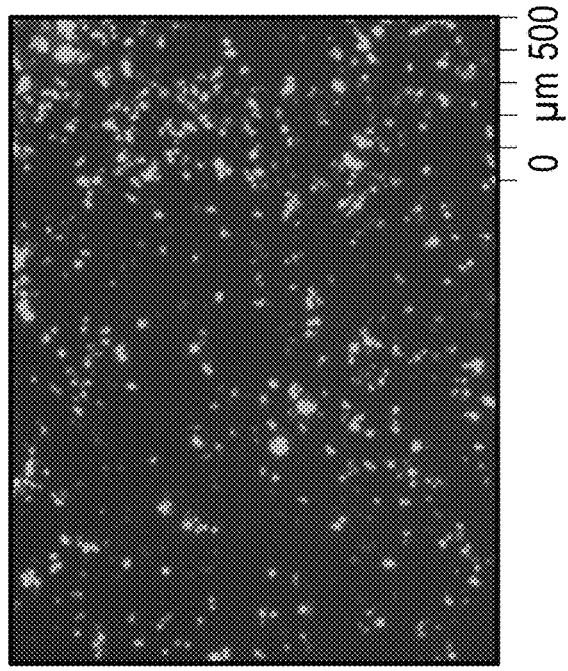
FIG. 4. Fluorescent microscope images depicting eGFP expression in PEI transfected HEK 293 T cells in serum free suspension culture. Panel A transfected with PEI 25,000 kDa; B transfected with PEI MAX (40,000 kDa); Panel C transfected with PEI pro. PEI Max resulted highest transfection efficiency.
Figure 4:
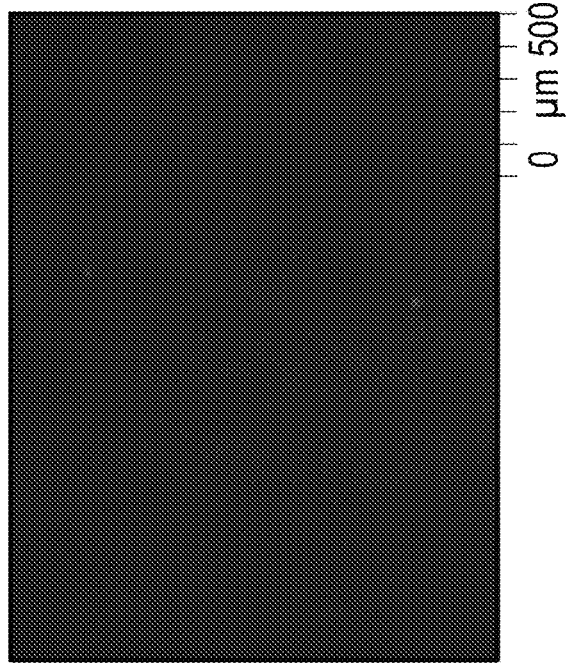
Figure 4:
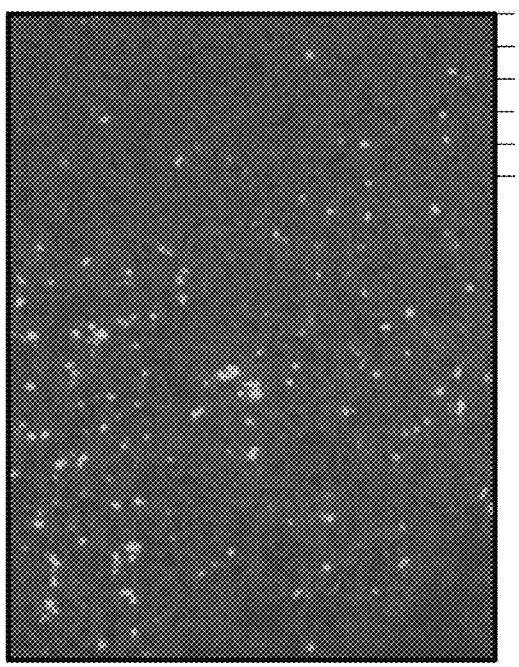
Figure 5:
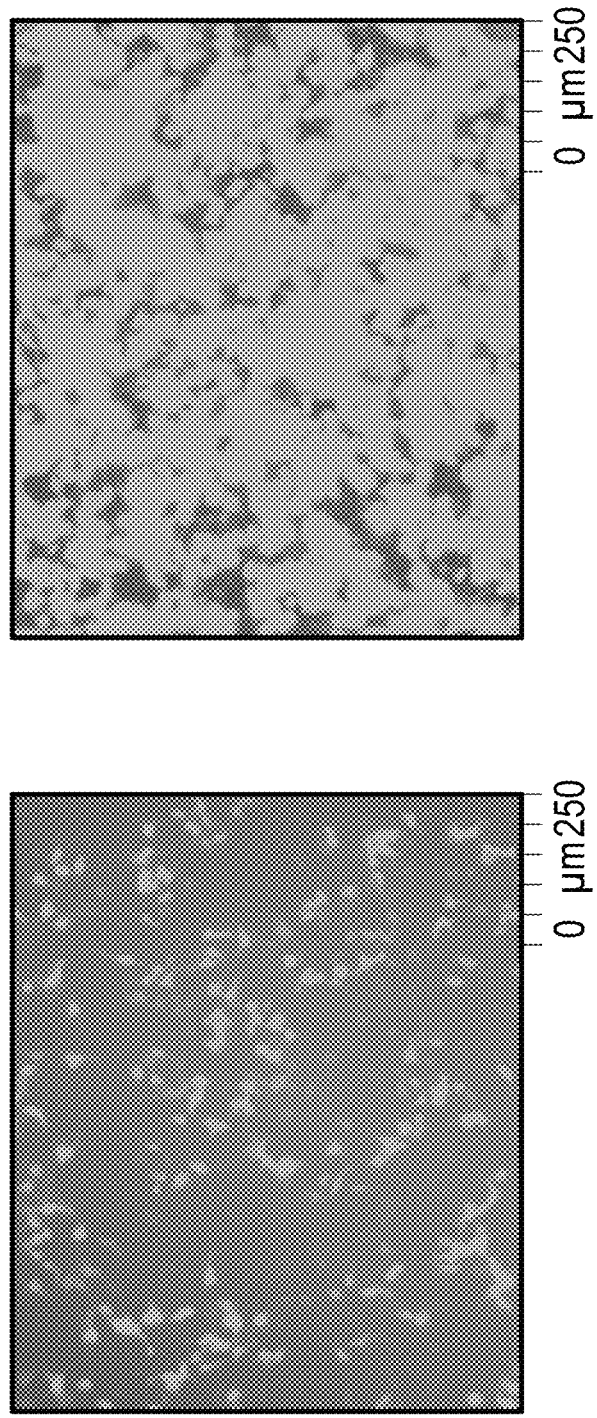
FIG. 5. Fluorescent microscope images depicting PEI transfection efficiency of HEK 293 T in serum free suspension culture (A) and lentiviral vector tranduction of HEK 293 cells. Panel A transfected using optimized condition with PEI MAX (40,000 kDa); Panel B shows lentivector transduction (50 ul harvested supernatant used).
Figure 6A:
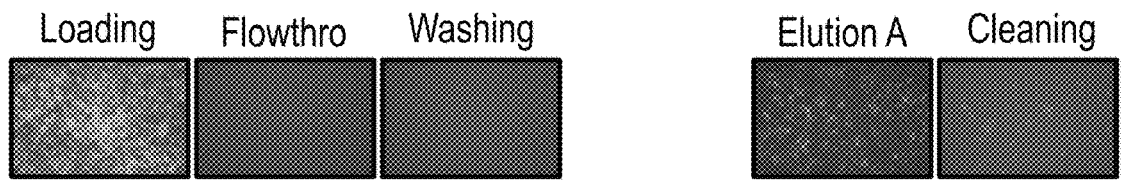
FIG. 6A-6E. Analysis of Lentivector recovery from DEAE column chromatography and PEG modulated DEAE column Chromatography. Top panel illustrates the eGFP expression of samples from column chromatography fractions. A: Chromatography does not contains PEG modulation; B, C and D contains additional washing step using 4% PEG (4K); 4% PEG (6K) and 8% PEG (4K). 100 ul of each fraction were used to transduce HEK293 cells, eGFP positive cells were detected using fluorescence microscope and FACS (Bottom Panel). Almost 100% Lentivectors were detected in the elution fractions.
Figure 6B:
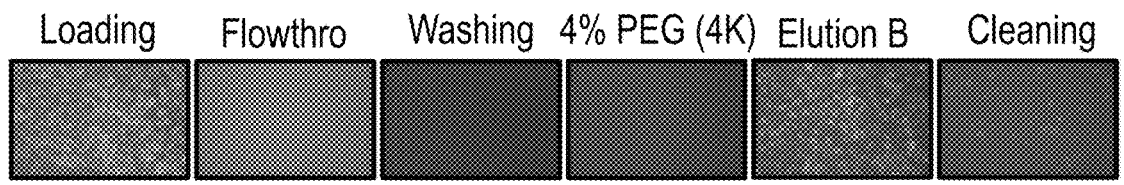
Figure 6C:
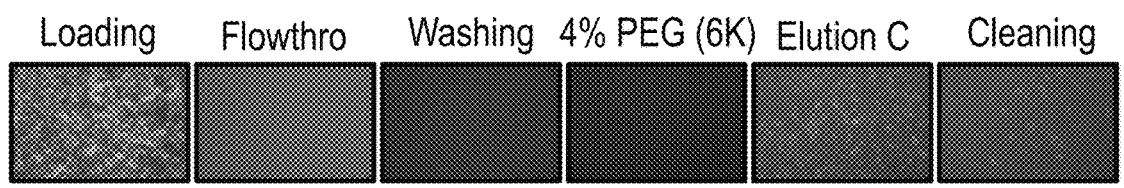
Figure 6D:
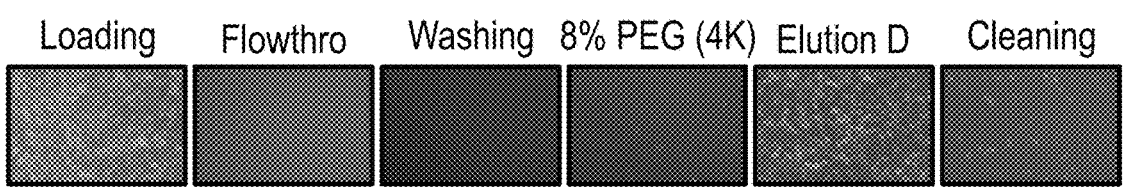
Figure 6E:
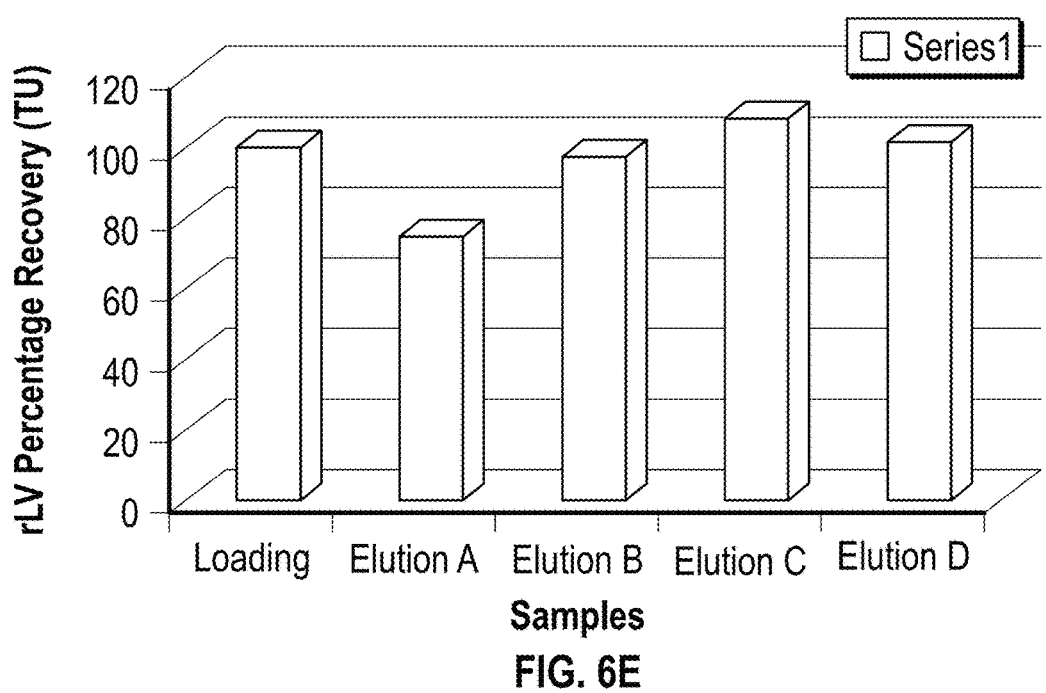
Figure 7A:
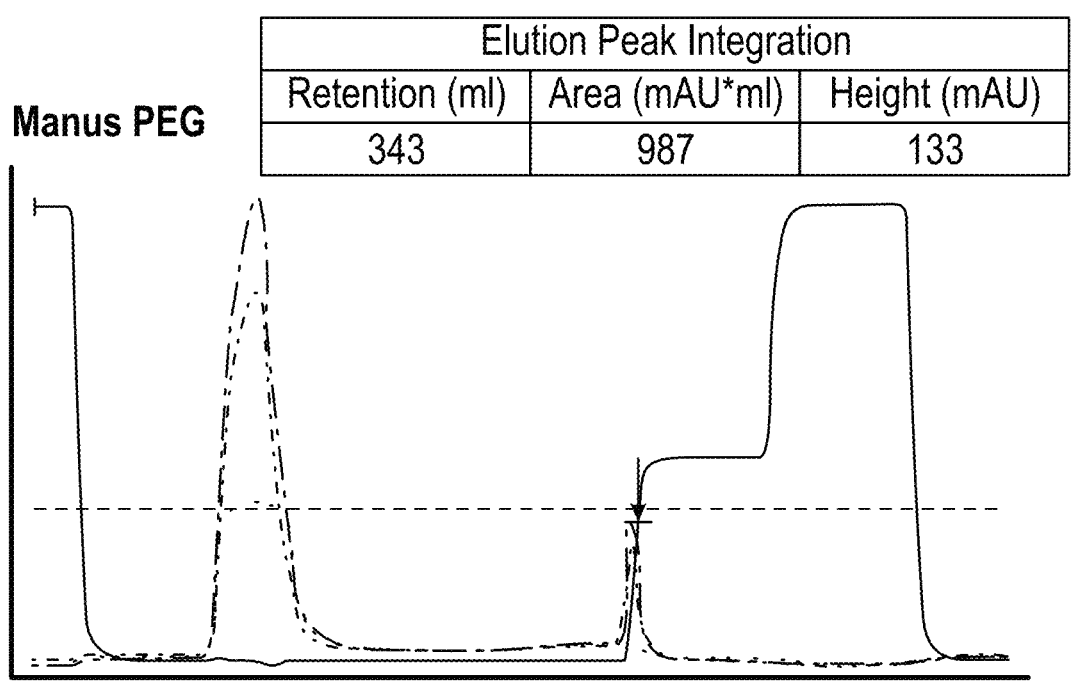
FIG. 7A-7D. Analysis of Lentivector elution using UV 280 nm absorption. 30 mls clarified lentivectors harvest were loaded on a 16 ml DEAE Sepharsoe FP column. Lentivectors were purified with PEG modulation (Panel B, C, D) or without PEG modulation (A). The vector elution peak was integrated using UV 280 nm absorption, the peak area reduce from 5 fold to almost 20 fold. It is interesting to note that UV absorption ratio of UV280/UV260 changed from UV280 dominant (panel A) to UV 260 dominant (panel B, C and D), indicating improved vector purity.
Figure 7B:
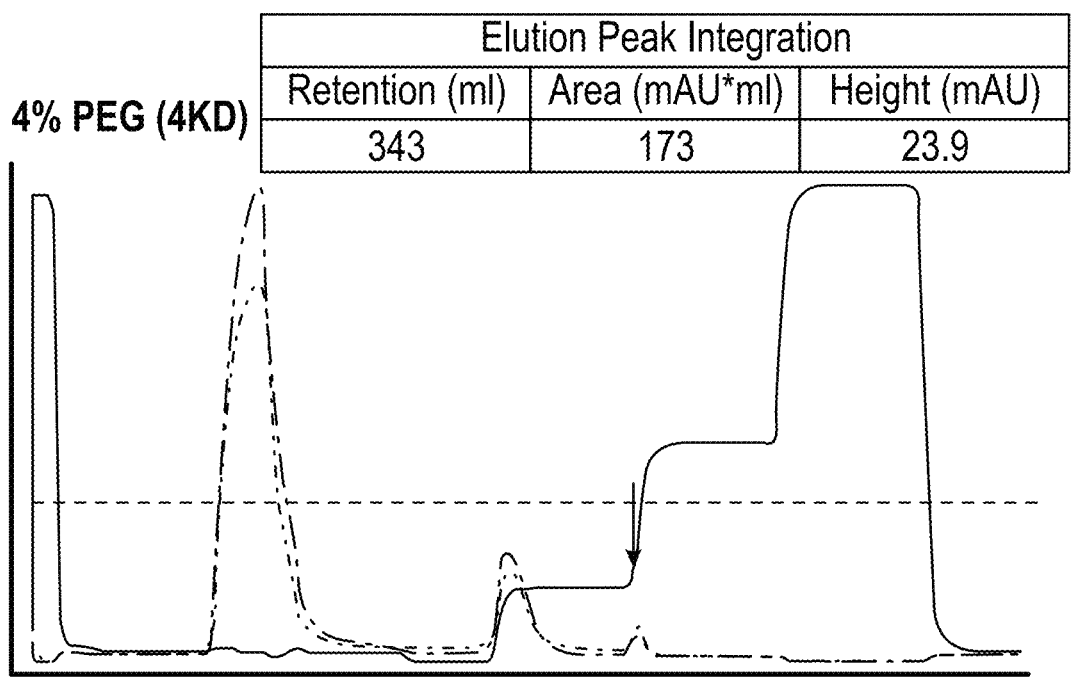
Figure 7C:
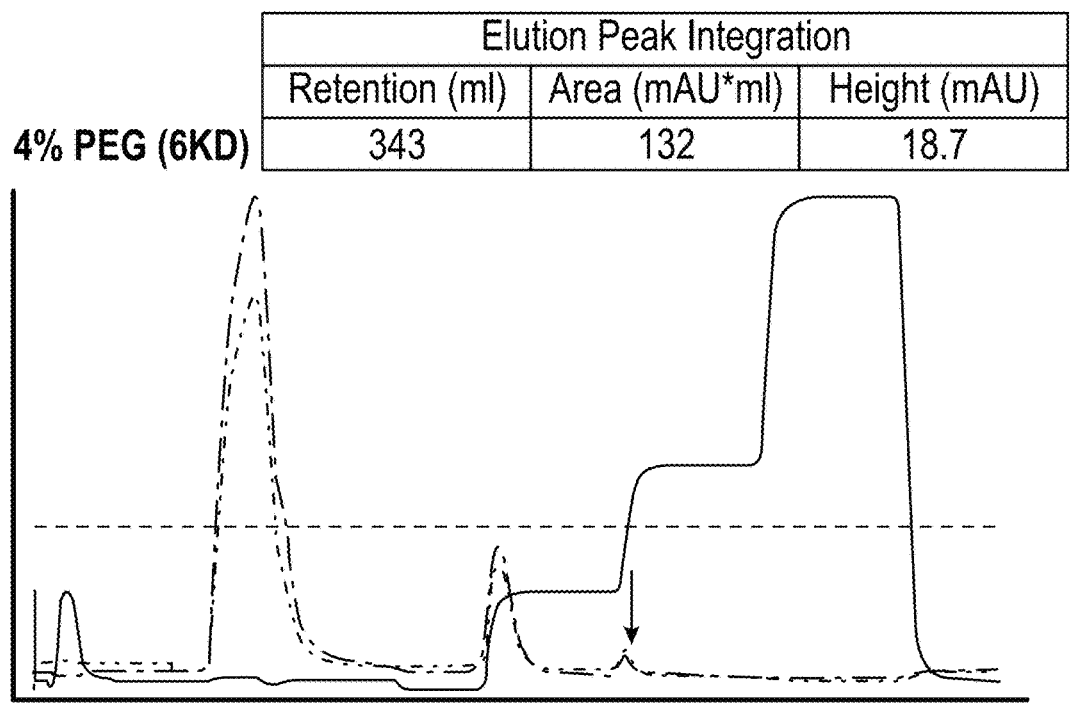
Figure 7D:
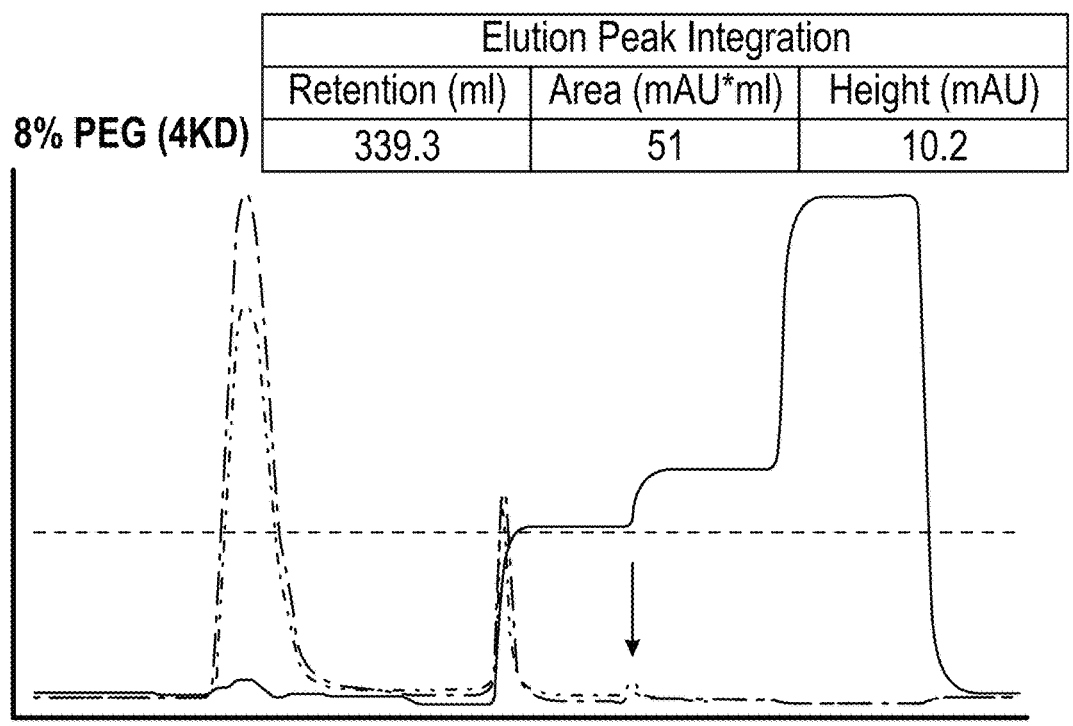

Polyethylenimine (PEI) is commercially available and was tested for efficient introduction of plasmid DNA into the newly adapted HEK 293T cells (6). Initial experiments revealed that the media selected for serum free cell culture did not support any transfection using PEI as transfection reagent, efforts were then directed to identify a serum free media that will support transfection of the cells using PEI. While one particular media type screened supported transfection (FIG. 3 Panel D), this media did not support suspension growth of the cells in long term cell culture (data not shown). We therefore design and developed a two step system to produce lentivectors in serum free suspension: First, cells are grown in the media that supports robust and rapid growth in suspension under serum free conditions. Second, the cell culture media is either replaced or mixed with a second media type that support PEI based transfection. In efforts to optimize PEI transfection efficiency, several deferent forms of PEI molecules from different commercial venders were evaluated. While small molecular weight linear PEI, such 25-kDa linear PEI has been used in several cases in manufacture of biological products (6), we hypothesis that branched PEI may exhibit greater delivery efficiencies for multiple plasmid transfections, due to the availability of multiple functional groups per molecule. Among the different PEI molecules evaluated, a small branched PEI, PEI MAX (40,000 kDa, Polysciences.com) resulted in the highest transfection efficiency of the adapted HEK 293T cells in the media identified (FIG. 4). Optimizing transfection condition using PEI MAX, we achieved almost one hundred percent cell transfection (FIG. 5 Panel A). Our preliminary semi-quantitative data indicated that lentiviral vectors were produced at the level about $1 \times 10^6$ transduction units per ml in the current production method. To the best of our knowledge, we believe the techniques innovated in our lab represent the first truly scalable lentivector production method in a serum free suspension cell culture system.

Further effort was made to improve vector specific productivity. Parameters, such as cell density at transfection, total DNA amount used for transfection, methods to prepare DNA/PEI complex, vector harvest time, were evaluated. The adapted HEK 293 T cells were cultured in CD293 media (complemented with 4 mM Glutamine) to the density of 3E+06/ml; the cell culture media was exchange to SFM4Transfx-293 (complemented with 4 mM Glutamine) (HyClone™, ThermoScientific) by either centrifugation and re-suspension or using tangential flow filtration technique, cell density was adjusted to 1.5E+06 cells per ml and incubated incubator. For the spinner flask cell culture, 130

RPM/min and 8% $CO_2$ were used. Total of 12 ug DNA was used to transfect 1.5E+06 cells and the DNA molar ratio of the four plasmids was 1:1:1:1. Polyethyleneimine"MAX" (Polysciences.com) was prepared using Tris buffered solution at concentration of 1 mg/ml and pH adjusted to 7.15. Mixture of DNA was added to PEI solution with mass ratio of 1:1, and the solution was mixed gently and further incubated shortly; the mixed DNA/PEI cocktail was further diluted using 5 mM Tris solution, pH 7.15; the final volume of the diluted DNA/PEI solution is 1/15 of the media of the cell culture to be transfected. The DNA/PEI solution was then added to the suspension cell culture at the volume ration of 1/15, the cell culture media was then harvested at 48 hours, 72 hours and 96 hours post transfection. HEK 293 cells were then transduced with the harvested cell culture harvests and analyzed for eGFP expression using FACS. Higher vector production was observed, more than 6E+06 TU/ml were produced in from plates and spinner flasks, a more scalable cell culture platform.

Figure 8:
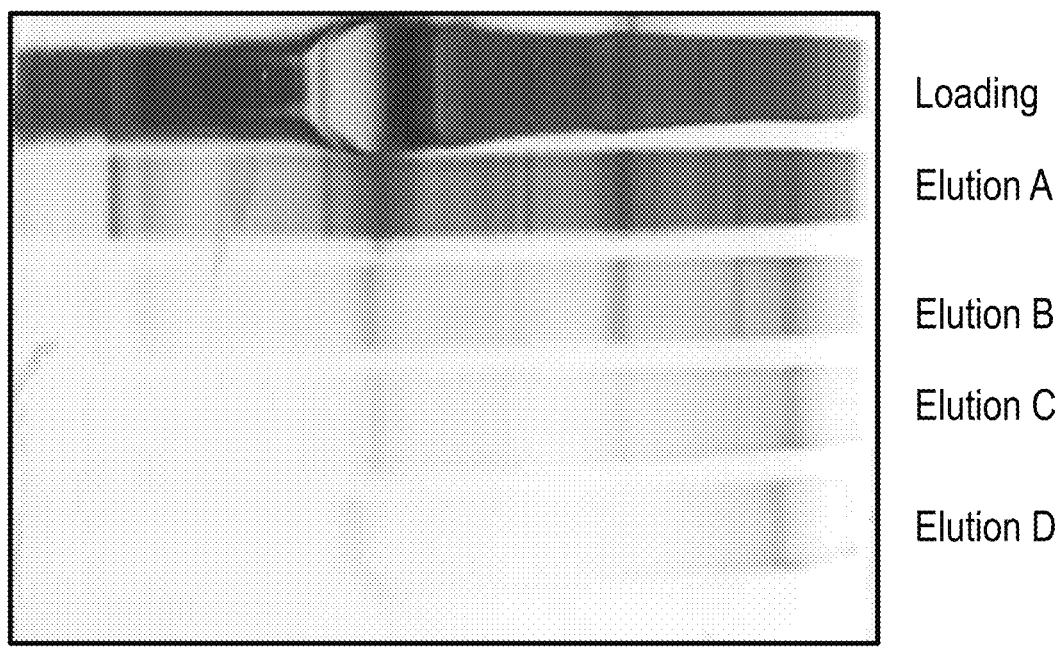
FIG. 8. SDS-PAGE Analysis of the Purity of Lentivector Eluted from Column Chromatography. 10 µl of each samples were loaded on a 4-12% NuePage Bis-Tris gel and silver stained after electrophoresis. Elution A is the sample of lentivector elution from column chromatography without PEG modulation; Elution B, C and D are the elution fractions from PEG-modulated column chromatography using 4% 4K PEG; 4% 6K PEG and 8% 4K PEG respectively. While the Lentivector recoveries are highly comparable for all of these eluted samples, the protein impurities are significantly reduced in the PEG-modulated fractions.
Figure 9:
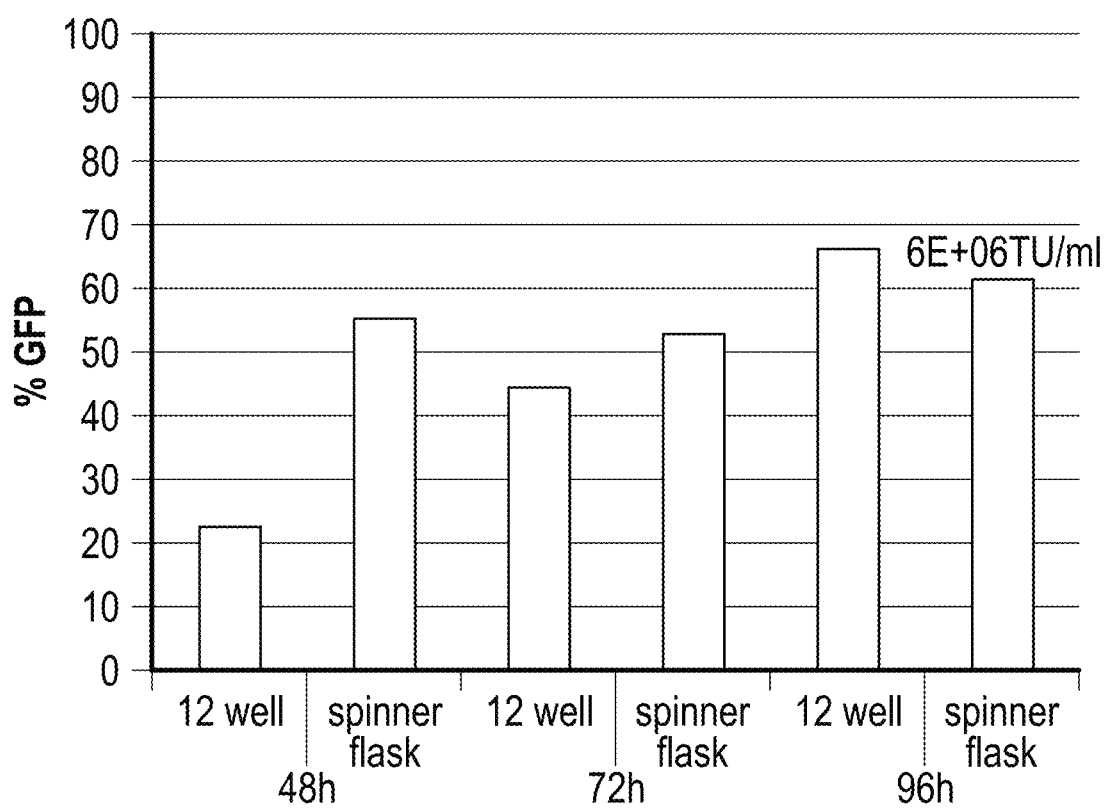
FIG. 9. FACS analysis of rLentivector productivity. Recombinant Lentivector expressing eGFP were produced using an optimized transfection method in serum-free suspension cell culture from 12 well-plates (1.5 ml cell culture) or spinner flask (40 ml cell culture). Vector yields were determined using FACS analysis. Vector productivity up to 6E+06 transduction units (TU) per milliliter were observed from both 12 well plates and spinner cell culture.

Column chromatography techniques are widely used in industry to purify large scale biological materials. Lentivectors are currently purified either by centrifugation techniques to precipitate the vectors (3) or by column chromatography techniques to isolate the particles (6). Column chromatography based processes address the scale issues in manufacture when using e classic centrifugation techniques, however, it still remains a challenge to isolate high purity lentivectors. In the typical anion exchanger column chromatography, the lentivector harvested was loaded onto the column, washed with low concentration of slat (such as 100 mM NaCl), then the vectors were eluted with high salt buffer (650 mM NaCl to 1M NaCl) (6). A lot of cellular proteins were co-eluted using this type of chromatography procedures (FIG. 8, Lane 2). We reported a PEG-modulated column chromatography procedure for purification of adeno-associated viral vectors (7), the purity of rAAV vector isolated from the PEG-modulated chromatography was significantly improved. We hypothesized that PEG-modulated chromatography should also be applicable to the separation of Lentivectors from cellular proteins to enhance the vector purity since the separation is based on the size of the molecules even though the resins used are not size exclusion resins.

A PEG-modulated column chromatography procedure was developed using DEAE Sepharose Fast Flow resins. Lentiviral vectors were recovered from this procedure at more than 95% of transduction units based on FACS analysis of eGFP expressing cells (FIG. 5), while the vector purities are improved 20 fold than the purities using traditional column chromatography (FIGS. 6 and 7). While we employed a weak anion exchanger resin to develop the PEG-modulated purification protocol for lentivectors, we believe the principles behind this protocol should apply to any column chromatography resins, including affinity resin, strong and weak anion exchangers, strong and weak cation exchangers and other resins, as long as the vector binds to the resin. Based on innovative PEG modulated column chromatography, a complete scalable purification process was designed and developed. A flow chart of the procedures described herein is provided in FIG. 1.

The techniques described above are fully scalable process steps that will enable manufacture of sufficient quantities of high quantity rLenti vectors that are needed to support the exciting clinical applications that are emerging. Surprisingly, the methods and rLV compositions produced surpasses currently available manufacturing capacity for lenti-viral vectors and satisfies investigational product quality requirements.

What is claimed is:

1. A method for obtaining purified recombinant lenti-viral (rLV) vectors comprising a transgene, comprising;
    a) providing cells producing said rLV vectors, wherein said cells are in serum free suspension culture; and harvesting said rLV vectors from said serum free suspension culture;
    b) clarifying the harvest of step a) via filtration;
    c) harvesting the filtrate from step b) and optionally exposing said filtrate to nuclease digestion to remove DNA/RNA impurities;
    d) subjecting the filtrate of step c) to PEG-modulated anion exchange column chromatography, thereby isolating said rLV vectors;
    e) further purifying the isolated rLV vectors obtained from step d) via tangential flow filtration to reduce the volume and exchange buffer;
    f) subjecting the rLV vectors obtained from step e) to size exclusion column chromatography to further purify said rLV vectors;
    g) subjecting the further purified rLV vectors of step f) to tangential flow filtration, thereby obtaining a rLV vector solution; and
    h) filtering the rLV vector solution obtained from step g) through a 0.2-0.5 um pore diameter filter; and
    i) collecting said filtered rLV vectors obtained from step h), thereby obtaining said purified rLV vectors.

2. The method of claim 1, wherein said rLV vector comprises a rLV selected from an HIV-1, an HIV-2, an HIV-1/HIV-2 pseudotype, an HIV-1/SIV, an FIV, a caprine arthritis encephalistis virus (CAEV), an equine infectious anemia virus, a bovine immunodeficiency virus, or a Vesucular Stomatitis Virus G-pseudotyped lentivirus (VSVG pseudotypede) vector.

3. The method of claim 1, wherein said transgene encodes a nucleic acid selected from the group consisting of a siRNA, an antisense molecule, an miRNA a ribozyme and a shRNA.

4. The method of claim 1, wherein said transgene encodes a gene product selected from the group consisting of insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor α (TGFα), platelet-derived growth factor (PDGF), insulin growth factors I and II (IGF-I and IGF-II), TGFβ, activins, inhibins, bone morphogenic protein (BMP), nerve growth factor (NGF), brain-derived neurotrophic factor (BDNF), neurotrophins NT-3 and NT4/5, ciliary neurotrophic factor (CNTF), glial cell line derived neurotrophic factor (GDNF), neurturin, agrin, netrin-1 and netrin-2, hepatocyte growth factor (HGF), ephrins, noggin, sonic hedgehog and tyrosine hydroxylase.

5. The method of claim 1, wherein said transgene encodes a gene product selected from the group consisting of thrombopoietin (TPO), interleukins (IL1 through IL-17), monocyte chemoattractant protein, leukemia inhibitory factor, granulocyte-macrophage colony stimulating factor, Fas ligand, tumor necrosis factor α, tumor necrosis factor β, interferons α, interferon β, interferon γ, stem cell factor, flk-2/flt3 ligand, IgG, IgM, IgA, IgD, IgE, chimeric immunoglobulins, humanized antibodies, single chain antibodies, T cell receptors, chimeric T cell receptors, single chain T cell receptors, G protein-coupled receptors (GPCRs), CCR5, class I MHC molecules, and class II MHC molecules.

6. The method of claim 1, wherein said transgene comprises a nucleic acid encoding a protein useful for correction of in born errors of metabolism, the nucleic acid selected from the group consisting of carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor V, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, retinal pigment epithelium-specific 65 kDa protein (RPE65), H-protein, T-protein, cystic fibrosis transmembrane regulator (CFTR), and dystrophin coding sequences.

7. The method of claim 1, wherein said transgene encodes a gene product selected from Factor VIII and Factor IX.

8. The method of claim 1, wherein said transgene encodes a tumor associated antigen (TAA).

9. The method of claim 1, wherein said transgene encodes a gene product selected from the group consisting of CAIX, CD19, CD20, CD20, CD22, CD30, CD33, CD44v7/8, CEA, EGF-RIII (epidermal growth factor receptor variant 3) EGP-2, erb-B2, erb-B2, 3, 4, FBP, fetal acetycholine receptor, GD2, Her2/neu, IL-13R-a2, KDR, k-light chain, LeY, L1 cell adhesion molecule, MAGE-A1, mesothelin, MUC1, NKG2D, oncofetal antigen (h5T4), PSCA, PSMA, mAb IgE targeted TAA, TAG-72 and VEGF-R2.

10. The method of claim 1, wherein said cells are mammalian cells.

11. The method of claim 1, wherein said cells are HEK 293T (ATCC), HEK293F (Life Technologies), HEK293 (ATCC), 293S (ATCC), BHK (ATCC), BHK-21 (ATCC), CHO (ATCC), CHO/dhFr– (ATCC), or CHO K1 (ATCC) cells.

12. The method of claim 1, wherein said serum free suspension culture comprises serum free cell growth medium.

13. The method of claim 12, wherein said serum free growth medium is selected from: FreeStyle™293 (Gibco®, Life Technologies), DMEM/F12 (Gibco®, Life Technologies), SFM4Transfx-293 (HyClone™, ThermoScientific), CDM4HEK293 (HyClone™, ThermoScientific), StemPro-34SFM (Gibco®, Life Technologies), FreeStyle F17 (Gibco®, Life Technologies), 293SFM II (Gibco®, Life Technologies), and CD293 (Gibco®, Life Technologies).

14. The method of claim 1, wherein said nuclease comprises an endonuclease, an exonuclease, or a combination thereof.

15. The method of claim 1, wherein said nuclease comprises a deoxyribonuclease, a ribonuclease, or a combination thereof.

16. The method of claim 1, wherein said nuclease comprises Benzonase™ or a DNase.

17. The method of claim 1, wherein said anion exchange column chromatography comprises a strong or a weak anion exchange column chromatography.

18. The method of claim 1, wherein said anion exchange column comprises a quarternized polyethyleneimine based resin; or a quaternary amine based resin.

19. The method of claim 1, wherein said anion exchange column comprises a polyethyleneimine based resin; a Diethylaminoethyl (DEAE) based resin; or a Diethylaminopropyl based resin.

20. The method of claim 1, wherein said anion exchange column comprises a Hydroxyapatite ((Cas(P04)3OH)2) based resin; a N-benzyl-n-methyletheanolamine based resin; or an Octylamine based resin.

21. The method of claim 1, wherein said PEG-modulated anion exchange column chromatography comprises:
   i) adjusting the filtrate of step c) to a binding solution, wherein said binding solution optionally comprises PEG, and contacting said filtrate with the anion exchange column thereby binding the rLV vectors to the anion exchange column,
   ii) washing the bound rLV vectors to remove impurities with a washing solution comprising PEG or a solution comprising PEG and a salt; and
   iii) eluting the rLV vectors from the anion exchange column with an elution solution.

22. The method of claim 21, wherein said binding solution comprises PEG in an amount from—0% to 10% weight/volume, or from 0% to 5% weight/volume, or from 0% to 2% weight/volume.

23. The method of claim 21, wherein said binding solution comprises PEG having a molecular weight from 2,000 kDa to 40,000 kDa.

24. The method of claim 21, wherein said washing solution comprises PEG in an amount from 1% to 10% weight/volume, or from 1% to 5% weight/volume, or from 1% to 2% weight/volume.

25. The method of claim 21, wherein said washing solution comprises PEG having a molecular weight from 2,000 kDa to 40,000 kDa.

26. The method of claim 21, wherein said elution solution comprises PEG in an amount from 0% to 20% weight/volume.

27. The method of claim 21, wherein said elution solution comprises PEG having a molecular weight from 2,000 kDa to 40,000 kDa.

28. The method of claim 21, wherein said binding, washing or elution solution further comprises a salt.

29. The method of claim 28, wherein said salt comprises sodium chloride or potassium chloride.

30. The method of claim 21, wherein said elution solution comprises salt in an amount from 500 mM to 1,000 mM.

31. The method of claim 1, wherein said filtering of step h) is through a 0.20 um pore diameter filter.

32. The method of claim 1, wherein said filtering of step h) is through a 0.22 um pore diameter filter.

33. The method of claim 1, wherein said filtering of step h) is through a 0.45 um pore diameter filter.

34. The method of claim 1, wherein said rLV vector collected at step i) is at $1 \times 10^5$ infectious units (IU)/ml to $1 \times 10^9$ infectious units (IU)/ml.

35. The method of claim 1, wherein said rLV vector collected at step i) is at $6 \times 10^6$ infectious units (IU)/ml+/−10%.

36. The method of claim 1, wherein said rLV vector collected at step i) is at $3 \times 10^8$ infectious units (IU)/ml+/−10%.

37. A method for obtaining purified recombinant rLV vectors comprising a transgene, comprising;

a) providing cells producing said rLV vectors, wherein said cells are in serum free suspension culture; and harvesting said rLV vectors from said serum free suspension culture;
b) clarifying the harvest of step a) via filtration;
c) subjecting the clarified suspension of step b) to tangential flow filtration to reduce volume and exchange buffer;
d) harvesting the filtrate from step c) and optionally exposing said filtrate to nuclease digestion to remove DNA/RNA impurities;
e) subjecting the filtrate of step d) to PEG-modulated anion exchange column chromatography, thereby isolating said rLV vectors;
f) subjecting the isolated rLV vectors obtained from step e) to size exclusion column chromatography to further purify said rLV vectors;
g) subjecting the further purified rLV vectors of step f) to tangential flow filtration, and thereby obtaining a rLV vector solution; and
h) filtering the rLV vector solution obtained from step g) through a 0.2-0.5 um pore diameter filter; and
i) collecting said filtered rLV vectors obtained from step h), thereby obtaining said purified rLV vectors.

38. A method for obtaining purified recombinant rLV vectors comprising a transgene, comprising;

a) providing cells producing said rLV vectors, wherein said cells are in serum free suspension culture; and harvesting said rLV vectors from said serum free suspension culture;
b) clarifying the harvest of step a) via filtration;
c) subjecting the clarified suspension of step b) to tangential flow filtration to reduce volume and exchange buffer;
d) harvesting the filtrate from step c) and optionally exposing said filtrate to nuclease digestion to remove DNA/RNA impurities;
e) subjecting the filtrate of step d) to PEG-modulated anion exchange column chromatography, thereby isolating said rLV vectors;
f) further purifying the isolated rLV vectors obtained from step e) via tangential flow filtration to reduce the volume and exchange buffer;
g) subjecting the rLV vectors obtained from step f) to size exclusion column chromatography to further purify said rLV vectors;
h) subjecting the further purified rLV vectors of step g) to tangential flow filtration, thereby obtaining a rLV vector solution; and
i) filtering the rLV vector solution obtained from step h) through a 0.2-0.5 um pore diameter filter; and
j) collecting said filtered rLV vectors obtained from step i), thereby obtaining said purified rLV vectors.

\* \* \* \* \*